United States Patent
Savory et al.

(10) Patent No.: US 9,499,510 B2
(45) Date of Patent: *Nov. 22, 2016

(54) PRO-DRUG COMPOUNDS

(71) Applicant: Proximagen Limited, London (GB)

(72) Inventors: Edward Savory, Cambourne (GB); Martyn Pritchard, St. Ives (GB); Mike Ashwood, London (GB)

(73) Assignee: Proximagen Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/410,234

(22) PCT Filed: Jul. 3, 2013

(86) PCT No.: PCT/GB2013/051767
§ 371 (c)(1),
(2) Date: Dec. 22, 2014

(87) PCT Pub. No.: WO2014/006407
PCT Pub. Date: Jan. 9, 2014

(65) Prior Publication Data
US 2015/0322034 A1     Nov. 12, 2015

(30) Foreign Application Priority Data

Jul. 3, 2012 (GB) .................... 1211788.3
Mar. 15, 2013 (GB) .................... 1304812.9

(51) Int. Cl.
C07D 311/70    (2006.01)
C07D 311/68    (2006.01)
C07F 9/655     (2006.01)

(52) U.S. Cl.
CPC ........... *C07D 311/70* (2013.01); *C07D 311/68* (2013.01); *C07F 9/65522* (2013.01)

(58) Field of Classification Search
CPC .................... C07D 311/70; C07F 9/65522
See application file for complete search history.

(56) References Cited

U.S. PATENT DOCUMENTS

| | | |
|---|---|---|
| 2014/0011773 A1 | 1/2014 | Savory et al. |
| 2014/0275068 A1 | 9/2014 | Savory et al. |
| 2016/0016929 A1 | 1/2016 | Savory et al. |

FOREIGN PATENT DOCUMENTS

| | | |
|---|---|---|
| EP | 0126311 A2 | 11/1984 |
| EP | 0139992 A1 | 5/1985 |
| EP | 0301713 A2 | 2/1989 |
| WO | 94/13657 | 6/1994 |
| WO | 9413656 A1 | 6/1994 |
| WO | 9521172 A1 | 8/1995 |
| WO | 95/34546 | 12/1995 |
| WO | 9534545 A1 | 12/1995 |
| WO | 00/00484 | 1/2000 |
| WO | 2006/071995 A1 | 7/2006 |
| WO | 2009/147441 A2 | 12/2009 |
| WO | 2009147442 A1 | 12/2009 |
| WO | 2011/067608 A1 | 6/2011 |
| WO | 2011067607 A1 | 6/2011 |
| WO | 2014140510 A1 | 9/2014 |

OTHER PUBLICATIONS

WebMD: Migrains and Headaches Health Center. (2014) <http://www.webmd.com/migraines-headaches/guide/migraine-treatments?page=2>. Retrieved on Sep. 11, 2015.
International Search Report for application PCT/GB2013/053423 filed Dec. 23, 2013.
United Kingdom Search Report for application GB 1304814.5 filed Mar. 15, 2013.
UKIPO Search Report dated Aug. 27, 2013 for patent application GB 1304812.9 filed Mar. 15, 2013.
UKIPO Search Report dated Oct. 18, 2012 for patent application GB 1211788.3 filed Jul. 3, 2012.
PCT International Search Report dated Aug. 8, 2013 for patent application PCT/GB2013/051767 filed Jul. 3, 2013.
Blower, Peter R. and Paul C. Sharpe. "Tonabersat," Innovative Drug Development for Headache Disorders: Frontiers in Headache Research, edited by Jes Olesen and Nabih Ramadan, Ramadan Oxford University Press, vol. 16, pp. 85-93, 2008.
Chan, Wai N. et al. "Conformational Preference of the 6-Acetyl Group in Novel Anticonvulsant trans 4S-benzamido-benzo[b]pyran-3R-OLS," Bioorganic & Medicinal Chemistry Letters, vol. 7, No. 12, pp. 1573-1576, 1997.
Chan, Wai N. et al. "Identification of (−)-cis-6-acetyl-4S-(3-chloro-4-fluoro-benzoylamino)-3,4-dihydro-2,2-dimethyl-2H-benzo[b]pyran-3S-OL as a Potential Antimigraine Agent," Bioorganic & Medicinal Chemistry, vol. 9, No. 2, pp. 285-290, 1999.
Chan, Wai N. et al. "Synthesis of Novel trans-4-(Substituted-benzamido)-3,4-dihydro-2H-benzo[b]-pyran-3-ol Derivatives as Potential Anticonvulsant Agents with a Distinctive Binding Profile," Journal of Medicinal Chemistry, vol. 39, No. 23, pp. 4537-4539, 1996.

(Continued)

*Primary Examiner* — Golam M M Shameem
(74) *Attorney, Agent, or Firm* — Sean B. Mahoney

(57) ABSTRACT

A compound of formula (I), or a pharmaceutically acceptable salt thereof: wherein $Z_1$, $Z_2$, and $Z_3$, Q, $R^2$, A, and $R^1$ are as defined in the claims.

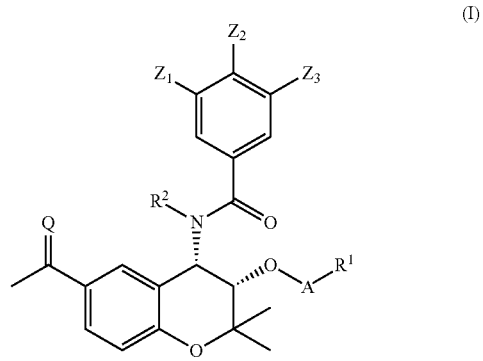

16 Claims, No Drawings

(56) References Cited

OTHER PUBLICATIONS

Huttunen, Kristiina M. et al. "Prodrugs—from Serendipity to Rational Design," Pharmacological Reviews, vol. 63, No. 3, pp. 750-771, 2011.
Huttunen, Kristiina M. et al. "Efficient Strategy to Prepare Water-Soluble Prodrugs of Ketones," Synlett, vol. 5, pp. 0701-0704, 2006, abstract only.
Kumpulainen, Hanna et al. "Evaluation of Hydroxyimine as Cytochrome P450-Selective Prodrug Structure," Journal of Medicinal Chemistry, vol. 49, No. 3, pp. 1207-1211, 2006, abstract only.
Maag, Hans. "Case Study: Valganciclovir: A Prodrug of Ganciclovir," Prodrugs: Challenges and Rewards, Part 1, edited by Valentino J. Stella et al, pp. 678-685, 2007.
Parsons, Andrew A. et al. "Tonabersat (SB-220453) a novel benzopyran with anticonvulsant properties attenuates trigeminal nerve-induced neurovascular reflexes," British Journal of Pharmacology, vol. 132, No. 7, pp. 1549-1557, 2001.
Pradeep, B. et al. "Valacyclovir: Development, Treatment and Pharmacokinetics," International Journal of Applied Biology and Pharmaceutical Technology, vol. I, No. 3, 1076-1083, 2010.
Rautio, Jarkko, ed. Prodrugs and Targeted Delivery: Towards Better ADME Properties, vol. 47, p. 45-46, 2011.
Rautio, Jarkko, et al. "Prodrugs: design and clinical application," Nature Reviews, vol. 7, pp. 255-270, Mar. 2008.
Stella, Valentino J., et al., eds. Prodrugs: Challenges and Rewards, Part 1, p. 220, 2007.
Testa, Bernard et al, eds. Hydrolysis in Drug and Prodrug Metabolism: Chemistry, Biochemistry, and Enzymology, p. 471, 2003.
Upton, Neil et al. 5 Benzo[b]pyranols and Related Novel Antiepileptic Agents, Progress in Medicinal Chemistry, vol. 37, pp. 177-200, 2000.
Xu, Q. Alan, et al. Analytical Methods for Therapeutic Drug Monitoring and Toxicology, p. 234, 2011.
U.S. Appl. No. 14/776,151, filed Sep. 14, 2015, Pro-Drug Compounds.
Sigma-Aldrich. "Unnatural Amino Acids & Derivatives." (2015.) Web, <https://sigmaaldrich.com/chemistry/chemistry-products.html?TablePage=16274965>.
Castañer, J. et al. Drugs of the Future, vol. 24, No. 10, 1999, pp. 1078.

PRO-DRUG COMPOUNDS

The present invention relates to neuronal gap junction blocking compounds having improved pharmacokinetic properties, the compounds being useful for the treatment or prevention of a range of conditions including migraine, epilepsy, non-epileptic seizures, brain injury (including stroke, intracranial haemorrhage and trauma induced) or cardiovascular disease including myocardial infarction, coronary revascularization or angina.

BACKGROUND TO THE INVENTION

Cortical spreading depolarization (CSD) is a wave of depolarisation with consequent depressed electrical activity which spreads across the surface of the cerebral cortex (at a rate of 2-6 mm/min) usually followed by hyperaemia and neuronal hyperpolarisation. The reduction in electrical activity is a consequence of neuron depolarisation and swelling, with K+ efflux, Na and Ca influx and electrical silence. This abnormal neuronal activity is associated with delayed neuronal damage in a number of pathological states including cerebral ischaemia (arising from e.g. stroke, haemorrhage and traumatic brain injury Strong et al., 2002 Fabricius et al., 2006; Dreier et al., 2006 Dohmen et al., 2008), epilepsy and the aura associated with migraine (Lauritzen 1994; Goadsby 2007). As the CSD wave moves across the cortex it is associated with a reactive increase in local blood flow which may serve to help restore the more normal ionic balance of the neurons affected. After the CSD induced hyperaemia the local increase in blood flow attenuates (oligaemia) potentially resulting in imbalances in energy supply and demand. Under certain conditions, the reactive hyperaemia is not observed, but instead the local vasculature constricts resulting in ischaemia which in turn can lead to neuronal death. The conditions triggering this abnormal response in experimental models are high extracellular levels of K+ and low NO availability. These conditions are typically seen in ischaemic areas of the brain, and clusters of CSD waves in these circumstances result in spreading ischaemia (see Dreier 2011). Of particular importance is the spreading ischaemia seen after sub-arachnoid haemorrhage (SAH), in the penumbra of an infarct and after traumatic brain injury where delayed neuronal damage can have a significant effect on clinical outcomes (Dreier et al., 2006, 2012; Hartings et al., 2011a, 2011b; Fabricius et al., 2006).

Given the detrimental effect of clusters of CSDs in humans and experimental animals, and the poor prognosis associated with CSDs, there is an unmet medical need for new compounds useful for inhibiting CSDs for patients with and without brain injuries. Without wishing to be bound by theory, the spread of CSD is believed to be mediated by gap junctions rather than by neuronal synaptic communication (Nedergard et al., 1995; Rawanduzy et al., 1997, Saito et al., 1997), the gap junctions providing a means of spreading the depolarisation in the absence of normal synaptic communication. Gap junctions are comprised of connexin proteins of which there are 21 in the human genome. Each Gap junction is made of two hemichannels, each comprising six connexin monomers.

Gap junctions are also implicated in a number of other disease states including hereditary diseases of the skin and ear (e.g. keratitis-ichthyosis deafness syndrome, erythrokeratoderma variabilis, Vohwinkel's syndrome, and hypotrichosis-deafness syndrome). Blockade of gap junction proteins has been shown to beneficial in some preclinical models of pain (e.g. Spataro et al., 2004 J Pain 5, 392-405, Wu et al., 2012 J Neurosci Res. 90, 337-45). This is believed to be a consequence of gap junction blockade in the spinal cord resulting in a reduction in the hypersensitivity of the dorsal horn to sensory nerve input. In addition gap junctions and their associated hemichannels have been implicated in neurodegenerative diseases including Alzheimer's disease, Parkinson's Disease, Huntington's Disease and amyotrophic lateral sclerosis (Takeuchi et al 2011 PLoS One.; 6, e21108).

Tonabersat (SB-220453/PRX201145) is a gap junction blocker (Silberstein, 2009; Durham and Garrett, 2009) which binds selectively and with high affinity to a unique stereo-selective site in rat and human brains. Consistent with its action on gap junctions Tonabersat also inhibits high K+ evoked CSD in cats (Smith et al., 2000; Read et al., 2000; Bradley et al., 2001) and rats (Read et al., 2001).

However, known gap junction blockers, including Tonabersat and Carabersat, suffer from undesirable physiochemical properties. Tonabersat is a crystalline solid with a high melting point (152-153 C) and with a relatively high lipophilicity (log P 3.32). The compound has no readily ionisable groups and consequently has a low aqueous solubility of 0.025 mg/ml over a range of pH values including pH of 7.4. The low aqueous solubility of Tonabersat makes both intravenous (IV) and oral (PO) modes of administration problematic. The poor aqueous solubility prevents rapid injection of the required dose of Tonabersat which is required for the treatment of head injuries and stroke or for emergency treatment of epileptic seizures where the patient may be unconscious and unable to swallow an oral drug. At present the effective plasma concentrations needed to reduce the cortical spreading depression caused by head injury or stroke can only be reached by slow IV infusion given over a period of hours. With respect to the PO administration of Tonabersat for the treatment of other indications, solubility limited dissolution of the tablet form of Tonabersat given PO leads to a significant "food effect" with differences in the maximum blood concentration of Tonabersat (Cmax) seen depending on whether the drug is given with or without food. These differences make it difficult to accurately predict the plasma exposure of Tonabersat when given orally, thus increasing the risk of under or over dosing the patient.

Therefore it is an object of the present invention to provide gap junction blocker compounds having improved physiochemical properties thus improving the utility of these agents in treating a range of disease states.

BRIEF DESCRIPTION OF THE INVENTION

The present invention makes available three classes of compounds, each class having one or more solubilising pro-drug groups.

DETAILED DESCRIPTION OF THE INVENTION

In a first aspect, the present invention makes available a class of compounds of formula (I) or a hydrate, solvate, or pharmaceutically acceptable salt thereof:

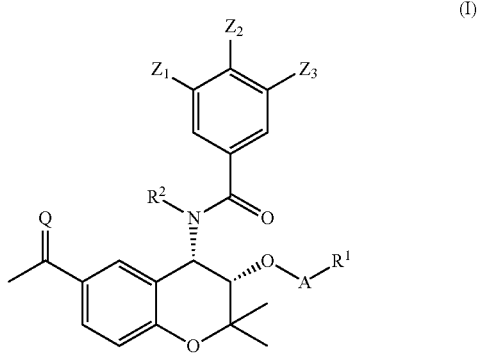

wherein $Z_1$, $Z_2$, and $Z_3$ are each independently selected from H, F, or Cl, Q is O, $R^2$ is H, A is a direct bond, —C(O)O*—, —C(R³)(R⁴)O*—, —C(O)O—C(R³)(R⁴)O*—, or —C(R³)(R⁴)O—C(O)O*— wherein the atom marked * is directly connected to $R^1$, $R^3$ and $R^4$ are selected independently from H, fluoro, $C_{1-4}$ alkyl, or $C_{1-4}$ fluoroalkyl, or $R^3$ and $R^4$ together with the atom to which they are attached form a cyclopropyl group, $R^1$ is selected from groups [1], [2], [2A], [2B] [3], [4], [5] or [6] wherein the atom marked ** is directly connected to A:

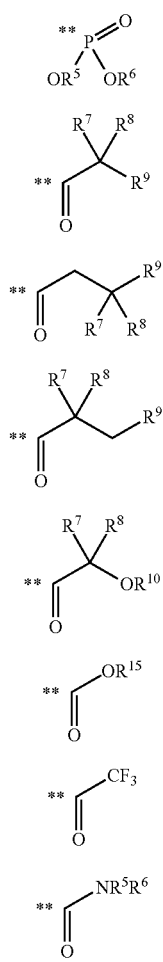

$R^5$ and $R^6$ are each independently selected from H, $C_{1-4}$ alkyl, $C_{1-4}$ fluoroalkyl, or benzyl;

$R^7$ is independently selected from H, $C_{1-4}$ alkyl, or $C_{1-4}$ fluoroalkyl;

$R^8$ is selected from:

(i) H, $C_{1-4}$ alkyl, or $C_{1-4}$ fluoroalkyl, or (ii) the side chain of a natural or unnatural alpha-amino acid; or $R^7$ and $R^8$ together with the atom to which they are attached form a $C_{3-7}$ carbocyclic ring;

$R^9$ is selected from H, —N($R^{11}$)($R^{12}$), or —N⁺($R^{11}$)($R^{12}$)($R^{13}$)X⁻, or —N($R^{11}$)C(O)$R^{14}$ wherein $R^{11}$, $R^{12}$, and $R^{13}$ are independently selected from H, $C_{1-4}$ alkyl, or $C_{1-4}$ fluoroalkyl, or $R^{11}$ and $R^{12}$ together with the nitrogen atom to which they are attached form a 3-8 membered heterocyclic ring, $R^{14}$ is H, $C_{1-4}$ alkyl, or $C_{1-4}$ fluoroalkyl, $R^{10}$ and $R^{15}$ are independently selected from $C_{1-4}$ alkyl or $C_{1-4}$ fluoroalkyl, X⁻ is a pharmaceutically acceptable anion.

In a second aspect, the present invention makes available a class of compounds of formula (II) or a hydrate, solvate, or pharmaceutically acceptable salt thereof:

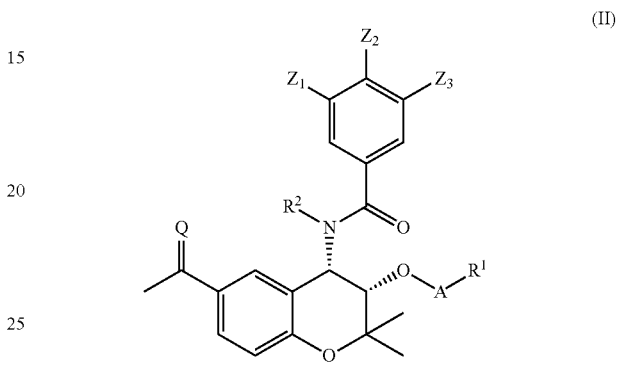

wherein $Z_1$, $Z_2$, and $Z_3$ are each independently selected from H, F, or Cl, Q is O, A is a direct bond and $R^1$ is H, $R^2$ is B—$R^{21}$ wherein, B is a direct bond, —C(O)O*—, C($R^{23}$)($R^{24}$)O*—, —C(O)O—C($R^{23}$)($R^{24}$)O*—, or —C($R^{23}$)($R^{24}$)O—C(O)*— wherein the atom marked * is directly connected to $R^{21}$, $R^{23}$ and $R^{24}$ are selected independently from H, fluoro, $C_{1-4}$ alkyl, or $C_{1-4}$ fluoroalkyl, or $R^{23}$ and $R^{24}$ together with the atom to which they are attached form a cyclopropyl group, $R^{21}$ is selected from groups [21], [22], [22A], [22B], [23], [24], [25] and [26] wherein the atom marked ** is directly connected to B:

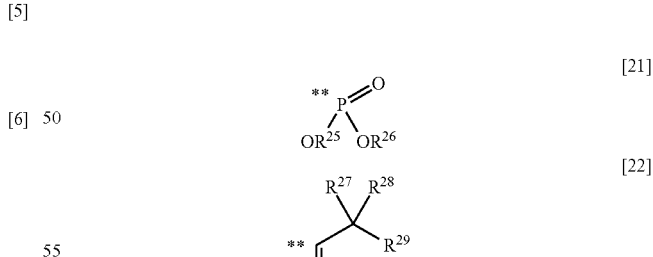

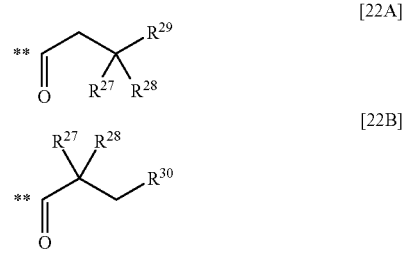

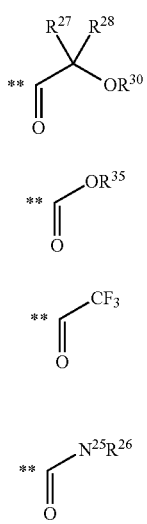

[23]

[24]

[25]

[26]

$R^{25}$ and $R^{26}$ are each independently selected from H, $C_{1-4}$ alkyl, $C_{1-4}$ fluoroalkyl or benzyl;

$R^{27}$ is independently selected from H, $C_{1-4}$ alkyl, $C_{1-4}$ fluoroalkyl;

$R^{28}$ is selected from:

(i) $C_{1-4}$ alkyl, or $C_{1-4}$ fluoroalkyl, or (ii) the side chain of a natural or unnatural alpha-amino acid;

or $R^{27}$ and $R^{28}$ together with the atom to which they are attached form a $C_{3-7}$ carbocyclic ring;

$R^{29}$ is selected from H, $-N(R^{31})(R^{32})$, or $-N^{+}(R^{31})(R^{32})(R^{33})X^{-}$, or $-N(R^{31})C(O)R^{34}$ wherein $R^{31}$, $R^{32}$, and $R^{33}$ are independently selected from H, $C_{1-4}$ alkyl, or $C_{1-4}$ fluoroalkyl, or $R^{31}$ and $R^{32}$ together with the nitrogen atom to which they are attached form a 3-8 membered heterocyclic ring, $R^{34}$ is H, $C_{1-4}$ alkyl, or $C_{1-4}$ fluoroalkyl, $X^{-}$ is a pharmaceutically acceptable anion, $R^{30}$ and $R^{35}$ are independently $C_{1-4}$ alkyl or $C_{1-4}$ fluoroalkyl.

In a third aspect, the present invention makes available a class of compounds of formula (IIIa) or (IIIb), or a hydrate, solvate, or pharmaceutically acceptable salt thereof:

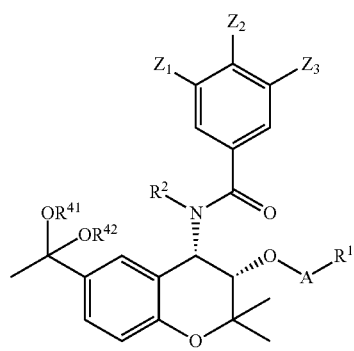
(IIIa)

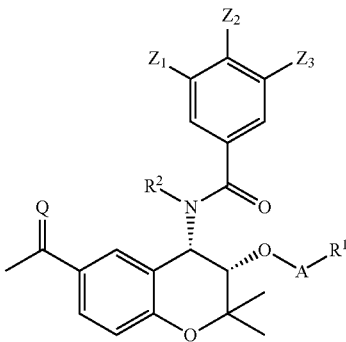
(IIIb)

wherein $Z_1$, $Z_2$, and $Z_3$ are each independently selected from H, F, or Cl; and $R^2$ and $-A-R^1$ are both H; and In the case of formula (IIIa):

$R^{41}$ and $R^{42}$ are independently H, $C_{1-4}$ fluoroalkyl or optionally substituted $C_{1-4}$ alkyl, or $R^{41}$ and $R^{42}$ together with the carbon atom to which they are attached form a 5-8 membered heterocycle, any carbon atom of which is optionally substituted; or In the case of formula (IIIb):

Q is an oxime of formula =NHOR$^{43}$, wherein R$^{43}$ is (i) selected from H, $C_{1-4}$ fluoroalkyl or optionally substituted $C_{1-4}$ alkyl, or (ii) -A$^{300}$-R$^{300}$ wherein A$^{300}$ is a direct bond, $-C(O)O^{*}-$, $-C(R^3)(R^4)O^{*}-$, $-C(O)O-C(R^3)(R^4)O^{*}-$, or $-C(R^3)(R^4)O-C(O)O^{*}-$ wherein the atom marked * is directly connected to R$^{300}$, R$^3$ and R$^4$ are selected independently from H, fluoro, $C_{1-4}$ alkyl, or $C_{1-4}$ fluoroalkyl, or R$^3$ and R$^4$ together with the atom to which they are attached form a cyclopropyl group, R$^{300}$ is selected from groups [1], [2], [2A], [2B], [3], [4], [5] or [6] wherein the atom marked ** is directly connected to A$^{300}$:

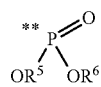
[1]

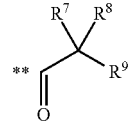
[2]

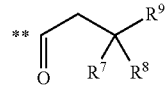
[2A]

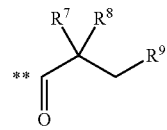
[2B]

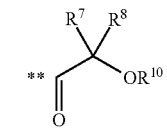
[3]

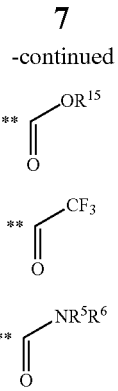

$R^5$ and $R^6$ are each independently selected from H, $C_{1-4}$ alkyl, $C_{1-4}$ fluoroalkyl, or benzyl;
$R^7$ is independently selected from H, $C_{1-4}$ alkyl, or $C_{1-4}$ fluoroalkyl;
$R^8$ is selected from:
(iii) H, $C_{1-4}$ alkyl, or $C_{1-4}$ fluoroalkyl, or
(iv) the side chain of a natural or unnatural alpha-amino acid;
or $R^7$ and $R^8$ together with the atom to which they are attached form a $C_{3-7}$ carbocyclic ring;
$R^9$ is selected from H, $-N(R^{11})(R^{12})$, or $-N^+(R^{11})(R^{12})(R^{13})X^-$, or $-N(R^{11})C(O)R^{14}$ wherein $R^{11}$, $R^{12}$, and $R^{13}$ are independently selected from H, $C_{1-4}$ alkyl, or $C_{1-4}$ fluoroalkyl, or $R^{11}$ and $R^{12}$ together with the nitrogen atom to which they are attached form a 3-8 membered heterocyclic ring,
$R^{14}$ is H, $C_{1-4}$ alkyl, or $C_{1-4}$ fluoroalkyl
$R^{10}$ and $R^{15}$ are independently selected from $C_{1-4}$ alkyl or $C_{1-4}$ fluoroalkyl,
$X^-$ is a pharmaceutically acceptable anion.

In an embodiment $R^{43}$ is $C_{1-4}$ alkyl optionally substituted with a phosphate group ($-P(O)OR^{61}R^{62}$). In an example of such an embodiment $OR^{43}$ is $-OCH_2P(O)OR^{61}OR^{62}$, wherein $R^{61}$ and $R^{62}$ are independently H or $C_{1-4}$ alkyl.

In another embodiment $R^{43}$ is an amino acid derivative having the structure $-C(O)CH(R^{100})NH_2$ wherein the group $R^{100}$ is the side chain of a natural or unnatural amino acid. In an embodiment $OR^{43}$ is $-OC(O)CH(CH(CH_3)_2)NH_2$.

Preferably the invention is as set out in the claims.

TERMINOLOGY

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein, the term "$(C_a-C_b)$fluoroalkyl" has the same meaning as "$(C_a-C_b)$alkyl" except that one or more of the hydrogen atoms directly connected to the carbon atoms forming the alkyl group is replaced by the corresponding number of fluorine atoms.

As used herein the unqualified term "carbocyclic" refers to a mono-, bi- or tricyclic radical having up to 16 ring atoms, all of which are carbon, and includes aryl and cycloalkyl.

As used herein the unqualified term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzothienyl, furyl, benzofuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, triazinyl, indolyl and indazolyl.

As used herein the unqualified term "heterocyclyl" or "heterocyclic" includes "heteroaryl" as defined above, and in addition means a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, $(C_1-C_6)$alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, halo (including fluoro, bromo and chloro), fully or partially fluorinated $(C_1-C_3)$alkyl, $(C_1-C_3)$alkoxy or $(C_1-C_3)$alkylthio such as trifluoromethyl, trifluoromethoxy, and trifluoromethylthio, nitro, nitrile ($-CN$), oxo, phenyl, phenoxy, monocyclic heteroaryl or heteroaryloxy with 5 or 6 ring atoms, tetrazolyl, $-COOR^A$, $-COR^A$, $-OCOR^A$, $-SO_2R^A$, $-CONR^AR^B$, $-SO_2NR^AR^B$, $-NR^AR^B$, $OCONR^AR^B$, $-NR^BCOR^A$, $-NR^BCOOR^A$, $-NR^BSO_2OR^A$ or $-NR^A-CONR^AR^B$ wherein $R^A$ and $R^B$ are independently hydrogen or a $(C_1-C_6)$alkyl group or, in the case where $R^A$ and $R^B$ are linked to the same N atom, $R^A$ and $R^B$ taken together with that nitrogen may form a cyclic amino ring, such as a morpholine, piperidinyl or piperazinyl ring. Where the substituent is phenyl, phenoxy or monocyclic heteroaryl or heteroaryloxy with 5 or 6 ring atoms, the phenyl or heteroaryl ring thereof may itself be substituted by any of the above substituents except phenyl, phenoxy, heteroaryl or heteroaryloxy. An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds of formula (I), (II), (IIIa) or (IIIb) which are basic can form salts, including pharmaceutically acceptable salts with inorganic acids, e.g. hydrohalic acids such as hydrochloric or hydrobromic acids, sulphuric acid, nitric acid or phosphoric acid and the like, and with organic acids e.g. acetic, tartaric, succinic, fumaric, maleic, malic, salicylic, citric, methanesulphonic, p-toluenesulphonic, benzoic, benzenesunfonic, glutamic, lactic, and mandelic acids and the like.

The formation of specific salt forms can provide compounds of the invention with improved physicochemical properties. For a review on suitable salts, see *Handbook of Pharmaceutical Salts: Properties, Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomers with R or S stereochemistry at each chiral axis. The invention includes all such enantiomers and diastereoisomers and mixtures thereof. In particular, the carbon atom to which the groups $R^7$ and $R^7$ are attached may be in either the R or the S configuration.

The compounds of the invention include compounds of formula (I), (II), (IIIa) or (IIIb) as hereinbefore defined, including all polymorphs and crystal habits thereof, prodrugs and isomers thereof (including optical, geometric and tautomeric isomers) as hereinafter defined and isotopically-labeled compounds of formula (I), (II), (IIIa) or (IIIb).

Also included within the scope of the invention are metabolites of compounds of formula (I), (II), (IIIa) or (IIIb), that is, compounds formed in vivo upon administration of the drug. Some examples of metabolites include:
(i) where the compound of formula I contains a methyl group, an hydroxymethyl derivative thereof ($-CH_3 \rightarrow -CH_2OH$);
(ii) where the compound of formula I contains an alkoxy group, an hydroxy derivative thereof ($-OR \rightarrow -OH$);
(iii) where the compound of formula I contains a tertiary amino group, a secondary amino derivative thereof (e.g. $-NR^{1A}R^{2A} \rightarrow -NHR^{1A}$ or $-NHR^{2A}$);
(iv) where the compound of formula I contains a secondary amino group, a primary derivative thereof ($-NHR^{1A} \rightarrow -NH_2$);
(v) where the compound of formula I contains a phenyl moiety, a phenol derivative thereof (-Ph→-PhOH); and
(vi) where the compound of formula I contains an amide group, a carboxylic acid derivative thereof ($-CONH_2 \rightarrow COOH$).

For use in accordance with the invention, the following structural characteristics are currently contemplated, in any compatible combination, in the compounds of formula (I):

The groups $Z_1$, $Z_2$, and $Z_3$ are each independently selected from H, F, or Cl. In an embodiment $Z_1$ is Cl, $Z_2$ is F, and $Z_3$ is H. In another embodiment $Z_1$ is Cl, $Z_2$ and $Z_3$ are H. In another embodiment $Z_1$ is H, $Z_2$ is F, and $Z_3$ is H. In another embodiment $Z_1$ is F, $Z_2$ is H, and $Z_3$ is F. The above definitions of $Z_1$, $Z_2$, and $Z_3$ is H are applicable to compounds of formula (I), (II), (IIIa), and (IIIb). As an illustration, the preferred definition of $Z_1$, $Z_2$, and $Z_3$ applied to the compounds of formula (I) is as follows:

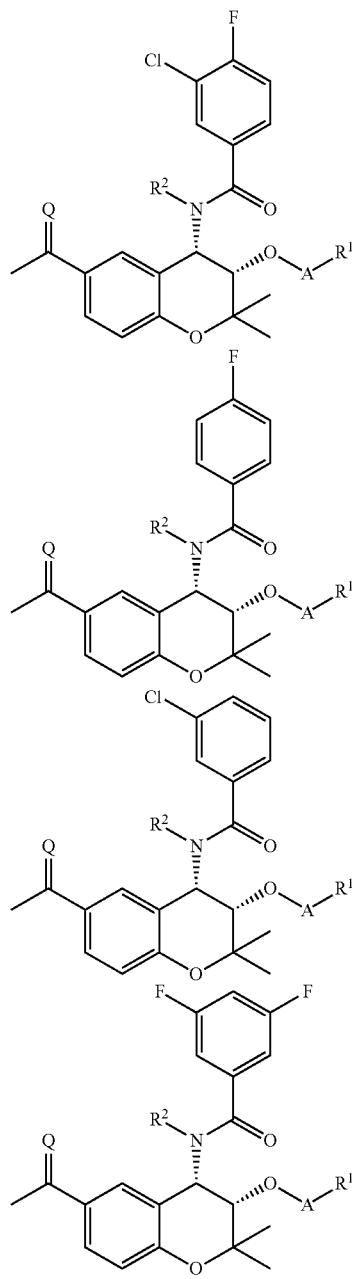

In a preferred embodiment $Z_1$ is Cl, $Z_2$ is F or H, and $Z_3$ is H.

The group Q is an oxygen atom

The group $R^2$ is a hydrogen atom

The group A is a direct bond, $-C(O)O^*-$, $-C(R^3)(R^4)O^*-$, $-C(O)O-C(R^3)(R^4)O^*-$, or $-C(R^3)(R^4)O-C(O)O^*-$ wherein the atom marked * is directly connected to $R^1$.

The groups $R^3$ and $R^4$ are selected independently from H, fluoro, $C_{1-4}$ alkyl such as methyl, ethyl, propyl or isopropyl, or $C_{1-4}$ fluoroalkyl such as trifluoromethyl, or $R^3$ and $R^4$ together with the atom to which they are attached form a cyclopropyl group, In an embodiment A is a direct bond. In another embodiment A is —CH$_2$O*—, or —CH(CH$_3$)O*—, or C(CH$_3$)$_2$O*—.

The group R$^1$ is selected from groups [1], [2], [2A], [2B], [3], [4], [5] or [6] wherein the atom marked ** is directly connected to A:

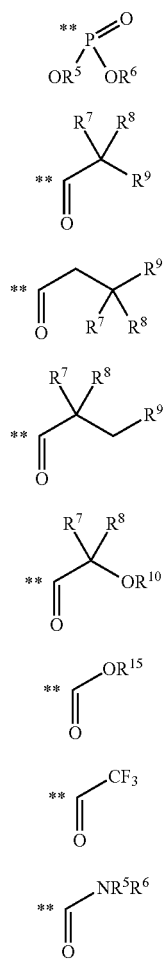

The groups R$^5$ and R$^6$ are each independently selected from H, C$_{1-4}$ alkyl such as methyl, ethyl, propyl or isopropyl, C$_{1-4}$ fluoroalkyl such as trifluoromethyl, or benzyl. In an embodiment R$^5$ and R$^6$ are hydrogen.

The group R$^7$ is independently selected from H, C$_{1-4}$ alkyl such as methyl, ethyl, propyl or isopropyl, or C$_{1-4}$ fluoroalkyl such as trifluoromethyl. In another embodiment R$^7$ and R$^8$ are both hydrogen, or R$^7$ is hydrogen and R$^8$ is methyl, or both R$^7$ and R$^8$ are methyl. In an embodiment R$^7$, R$^8$ and R$^9$ are hydrogen. In an embodiment R$^7$ is hydrogen.

The group R$^8$ is selected from:
(i) H, C$_{1-4}$ alkyl such as methyl, ethyl, propyl, or isopropyl, or C$_{1-4}$ fluoroalkyl such as trifluoromethyl, or
(ii) the side chain of a natural or unnatural alpha-amino acid;
or R$^7$ and R$^8$ together with the atom to which they are attached form a C$_{3-7}$ carbocyclic ring such as cyclopropyl, cyclobutyl, cyclopentyl or cyclohexyl;

The term "side chain of a natural or non-natural alpha-amino acid" refers to the group R$^{100}$ in a natural or non-natural amino acid of formula NH$_2$—CH(R$^{100}$)—CO$_2$H.

In an embodiment the group -AR$^1$ is selected from the following groups wherein the atom marked ** is directly connected to the oxygen atom of the parent drug:

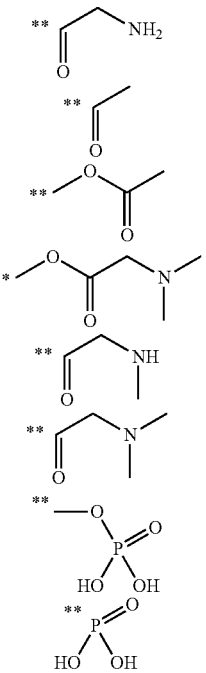

Examples of side chains of natural alpha amino acids include those of alanine, arginine, asparagine, aspartic acid, cysteine, cysteine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When R$^8$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a C$_1$-C$_6$ alkyl ester), amino groups may be converted to amides (for example as a NHCOC$_1$-C$_6$ alkyl amide) or carbamates (for example as an NHC(═O)OC$_1$-C$_6$ alkyl or NHC(═O)OCH$_2$Ph carbamate), hydroxyl groups may be converted to ethers (for example an OC$_1$-C$_6$ alkyl or a O(C$_1$-C$_6$ alkyl)phenyl ether) or esters (for example a OC(═O)C$_1$-C$_6$ alkyl ester) and thiol groups may be converted to thioethers (for example a tert-butyl or benzyl thioether) or thioesters (for example a SC(═O)C$_1$-C$_6$ alkyl thioester).

Examples of side chains of non-natural alpha amino acids include:
an optional substituent, C$_1$-C$_6$ alkyl, phenyl, 2, -3-, or 4-hydroxyphenyl, 2, -3-, or 4-methoxyphenyl, 2, -3-, or 4-pyridylmethyl, benzyl, phenylethyl, 2-, 3-, or 4-hydroxybenzyl, 2, -3-, or 4-benzyloxybenzyl, 2, -3-, or 4-$C_1$-$C_6$ alkoxybenzyl, and benzyloxy($C_1$-$C_6$alkyl)-groups, wherein any of the foregoing non-natural amino acid side chains is optionally substituted in the alkyl, phenyl or pyridyl group; or groups -[Alk]$_n$R$_{50}$ where Alk is a ($C_1$-$C_6$)alkyl or ($C_2$-$C_6$) alkenyl group optionally interrupted by one or more —O—, or —S— atoms or —N(R$_{51}$)— groups [where R$_{51}$ is a hydrogen atom or a ($C_1$-$C_6$)alkyl group], n is 0 or 1, and R$_{50}$ is an optionally substituted cycloalkyl or cycloalkenyl group; or a heterocyclic($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$) alkylamino, di-($C_1$-$C_6$)alkylamino, mercapto, ($C_1$-$C_6$)alkylthio, hydroxy($C_1$-$C_6$)alkyl, mercapto($C_1$-$C_6$)alkyl or ($C_1$-$C_6$)alkylphenylmethyl; and The group R$^9$ is selected from H, —N(R$^{11}$)(R$^{12}$) such as —NH$_2$, NH(CH$_3$), —NH(CH$_3$)$_2$, or —N$^+$(R$^{11}$)(R$^{12}$)(R$^{13}$)X$^-$ such as —N$^+$(CH$_3$)$_3$X$^-$, or —N(R$^{11}$)C(O)R$^{14}$ wherein R$^{11}$, R$^{12}$, and R$^{13}$ are independently selected from H, $C_{1-4}$ alkyl such as methyl, ethyl, propyl or isopropyl, or $C_{1-4}$ fluoroalkyl such as trifluoromethyl, or R$^{11}$ and R$^{12}$ together with the nitrogen atom to which they are attached form a 3-8 membered heterocyclic ring such as pyrrolidine, piperidine, piperazine, morpholine or homomorpholine. In an embodiment R$^{11}$ and R$^{12}$ are both methyl.

R$^{14}$ is H, $C_{1-4}$ alkyl such as methyl, ethyl, propyl or isopropyl, or $C_{1-4}$ fluoroalkyl such as trifluoromethyl R$^{10}$ and R$^{15}$ are independently selected from $C_{1-4}$ alkyl or $C_{1-4}$ fluoroalkyl.

The counterion X$^-$ is a pharmaceutically acceptable anion such as chloride, or any other anion fromed by removal of one or more protons from an inorganic acid, e.g. hydrohalic acids such as hydrochloric or hydrobromic acids, sulphuric acid, nitric acid or phosphoric acid and the like, or from an organic acids e.g. acetic, tartaric, succinic, fumaric, maleic, malic, salicylic, citric, methanesulphonic, p-toluenesulphonic, benzoic, benzenesunfonic, glutamic, lactic, and mandelic acids and the like.

Specific compounds of the invention include those of the Examples herein.

It will be understood that the compounds of formula (I), (II), (IIIa) or (IIIb) may be further modified by adding one or more of the prodrug groups Q, -AR$^1$ or R$^2$. For example the compounds of formula (I) or (II) may be modified by exchanging the oxygen atom Q for a prodrug Q group as defined in (IIIa) or (IIIb). Alternatively, the compounds of formula (I) could be modified by replacing the hydrogen atom R$^2$ by the prodrug group R$^2$ as defined in formula (II), and vice versa.

The present invention makes available a pharmaceutical composition comprising a compound of formula (I), (II), (IIIa) or (IIIb) together with one or more pharmaceutically acceptable carriers and/or excipients.

The present invention makes available a compound of formula (I), (II), (IIIa) or (IIIb) for use in medicine.

In an embodiment the inventions encompasses the use of a compound of formula (I), (II), (IIIa) or (IIIb) treatment of a disease or medical condition which benefits from inhibition of gap junction activity. Inhibition of gap junction activity may be achieved by blocking the gap junction as a whole or by blocking one or more hemichannels.

In an embodiment the inventions encompasses a method of treatment of a disease or medical condition which benefits from inhibition of gap junction activity, comprising administering to a subject suffering from such disease or condition and effective amount of a compound of formula (I), (II), (IIIa) or (IIIb).

In an embodiment the disease or condition which benefits from inhibition of gap junction activity is selected from among migraine, aura with or without migraine, epilepsy, non-epileptic seizures, cerebrovascular accidents including stroke, intracranial haemorrhage (including traumatic brain injury, epidural hematoma, subdural hematoma and subarachnoid haemorrhage), and intra-cerebral haemorrhage, spinal cord vascular accidents arising from trauma, epidural hematoma, subdural hematoma or subarachnoid haemorrhage, pain including pain arising from hyperalgesia caused by damage to sensory neurons (i.e. neuropathic pain including but not limited to diabetic neuropathy, polyneuropathy, cancer pain, fibromyalgia, myofascial pain, post herpetic neuralgia, spinal stenosis, HIV pain, post-operative pain, post-trauma pain) or inflammation (including pain associated with osteoarthritis, rheumatoid arthritis, sciatica/radiculopathy, pancreatitis, tendonitis), neurodegenerative disease (including but not limited to Alzheimer's Disease, Parkinson's Disease, Huntington's Disease and Amyotrophic Lateral Sclerosis) and cardiovascular disease including myocardial infarction, coronary revascularization or angina.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. However, for administration to human patients, the total daily dose of the compounds of the invention may typically be in the range 1 mg to 1000 mg depending, of course, on the mode of administration. For example, oral administration may require a total daily dose of from 10 mg to 1000 mg, while an intravenous dose may only require from 1 mg to 500 mg. The total daily dose may be administered in single or divided doses and may, at the physician's discretion, fall outside of the typical range given herein. These dosages are based on an average human subject having a weight of about 60 kg to 100 kg. The physician will readily be able to determine doses for subjects whose weight falls outside this range, such as infants and the elderly, and especially obese patients.

The compounds with which the invention is concerned may be prepared for administration by any route consistent with their pharmacokinetic properties. Suitable routes for administration include oral, intravenous, buccal, intranasal, inhalation, rectal, and intradermal. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The pro-drug may also be administered parenterally in a sterile medium. Depending on the vehicle and concentration used, the drug can either be suspended or dissolved in the vehicle. Advantageously, adjuvants such as local anaesthetic, preservative and buffering agents can be dissolved in the vehicle. The person skilled in the art is aware of many excipients useful for IV formulation.

PREPARATION OF COMPOUNDS OF THE INVENTION

The compounds of formula (I) above may be prepared by, or in analogy with, conventional methods. The preparation of intermediates and compounds according to the Examples of the present invention may in particular be illuminated by the following Schemes. Definitions of variables in the structures in Schemes herein are commensurate with those of corresponding positions in the formulas delineated herein.

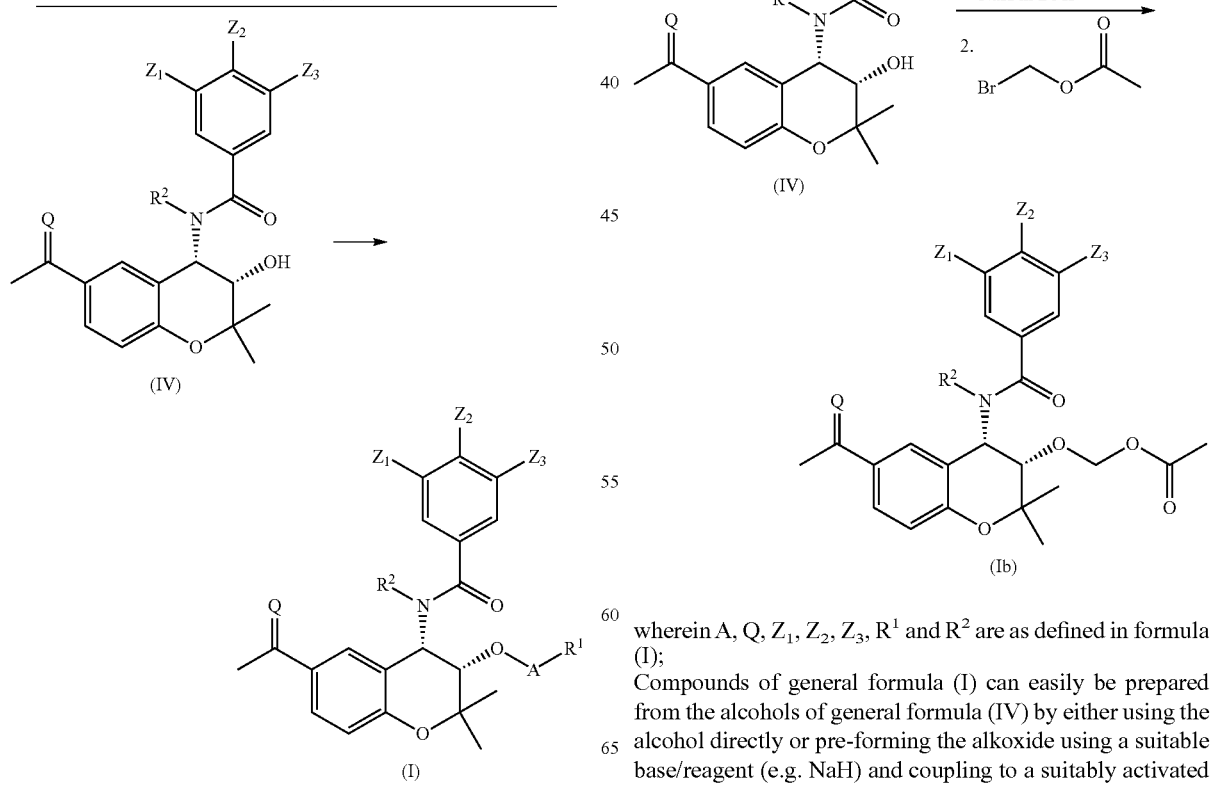

wherein A, Q, $Z_1$, $Z_2$, $Z_3$, $R^1$ and $R^2$ are as defined in formula (I);

Compounds of general formula (I) can easily be prepared from the alcohols of general formula (IV) by either using the alcohol directly or pre-forming the alkoxide using a suitable base/reagent (e.g. NaH) and coupling to a suitably activated A-R or R group (or protected A-R or R group). Activated A-R or R group functionalities typically used for the formation of phosphates, esters, carbonates and carbamates include, but not limited to, phosphoryl chlorides, acid chlorides, activated carboxylic acids, chloroformates, activated carbonates and isocyanates. The formation of (Ia) from (IV) using dimethylaminoacetyl chloride as an activated R group is representative of this approach. When the compound of general formula (I) has an A group defined as —$C(R^3)(R^4)O^*$— or $C(R^3)(R^4)OC(O)O^*$— these may be prepared from compounds of general formula (IV) using an appropriate alkylating agent which may include, but not limited to, alkylchlorides, alkylbromides, alkyliodides, mesylates and tosylates. The formation of (Ib) from (IV) using NaH to form the sodium alkoxide of (IV) followed by coupling with bromomethyl acetate as an activated A-R group is representative of this approach.

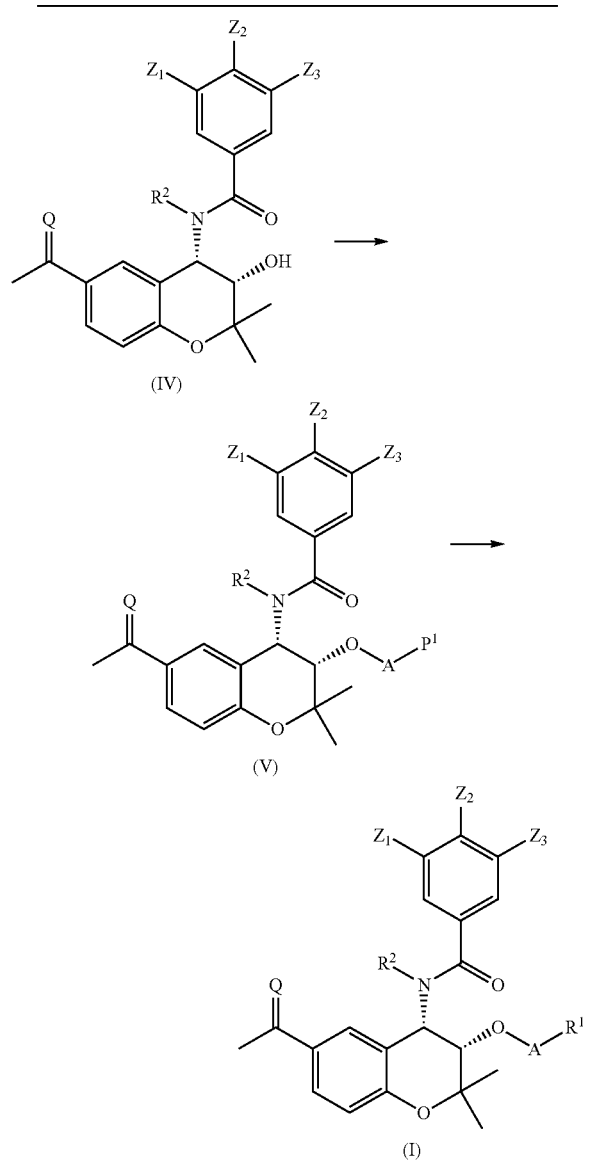

Scheme 2. General synthetic route for preparation of compounds of formula (I)

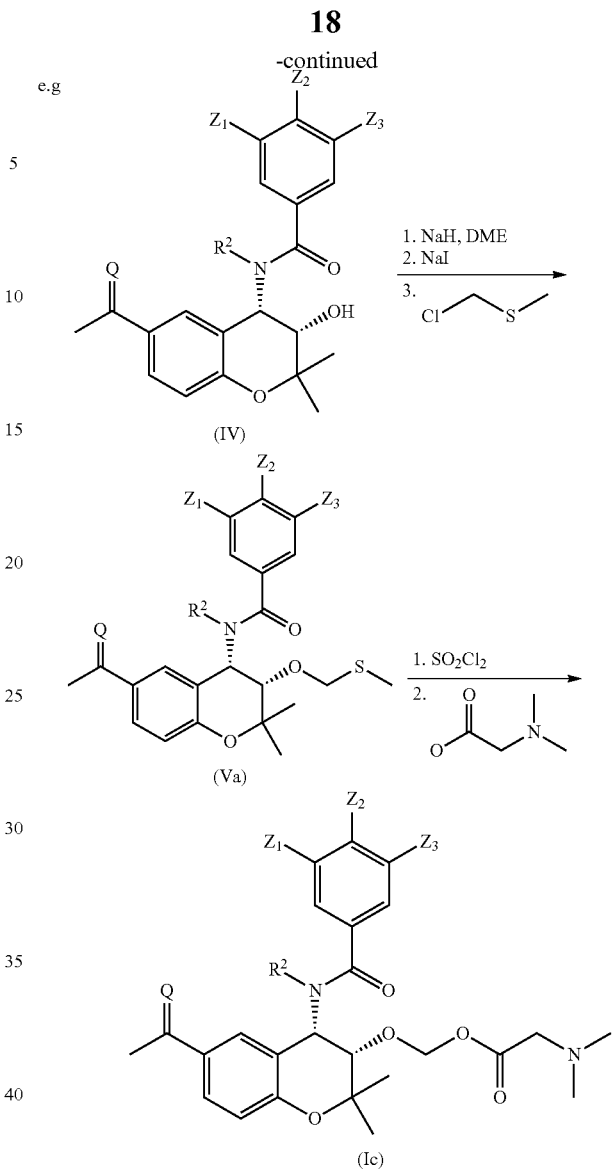

wherein A, Q, $Z_1$, $Z_2$, $Z_3$, $R^1$ and $R^2$ are as defined in formula (I);

$P^1$ is a suitable protecting group or functionality that can be readily chemically modified/utilised to append $R^1$.

Alternatively, compounds of general formula (I) can easily be prepared in a more step wise manner from the alcohol of general formula (IV) by using either the alcohol directly or pre-forming the alkoxide using a suitable base/reagent (e.g. NaH) and coupling to a suitably activated A-$P^1$ group. When the compound of general formula (I) has an A group defined as —$C(R^3)(R^4)O^*$— or $C(R^3)(R^4)OC(O)O^*$— these may be prepared using activated forms of A-$P^1$ including, but not limited to, alkylchlorides, alkylbromides, alkyliodides, mesylates and tosylates. When the compound of general formula (I) has an A group defined as —$C(O)O^*$— or $C(O)OC(R^3)(R^4)O^*$— these may be prepared using activated forms of A-$P^1$ including, but not limited to, chloroformates and activated carbonates. Then using methods known to those skilled in the art the intermediates of general formula (V) can be chemically modified to provide functionality that facilitates the final coupling step to afford compounds of general formula (I). The formation of (Ic)

from (IV) via the methylsulfanyl methoxy intermediate (Va) is representative of this approach.

The synthesis of Tonabersat, and other structurally related compounds, is disclosed in WO 95/34545. The present invention encompasses compounds prepared by applying the pro-drug groups -AR¹, R² and Q taught herein to the specific Examples disclosed in WO 95/34545. The methods proposed for the synthesis of compounds of general formula (I) are known to those skilled in the art, for example in Rautio et al., Nature Reviews Drug Discovery, 7, 255-270, 2008.

Optionally, a compound of formula (I) can also be transformed into another compound of formula (I) in one or more synthetic steps.

The following abbreviations have been used:
Boc tertiary-butyloxycarbonyl
D day(s)
calcd calculated
DCM dichloromethane
DIPEA diisopropylethylamine
DMAP 4-dimethylaminopyridine
DME dimethoxyethane
DMF dimethylformamide
EDC 1-ethyl-3-(3-dimethylaminopropyl)carbodiimide
ES+ electrospray ionization
EtOAc ethyl acetate
Et$_2$O diethyl ether
Et$_3$N triethylamine
EtOH ethanol
h hour(s)
HOBt Hydroxybenzotriazole
HPLC High Performance Liquid Chromatography
HRMS High-Resolution Mass Spectrometry
IMS Industrial methylated spirit
LCMS Liquid Chromatography Mass Spectrometry
Leu Leucine
M molar
MeCN acetonitrile
MeOH methanol
MTBE methyl tertiary-butyl ether
[MH]⁺ protonated molecular ion
min minute(s)
MS Mass Spectrometry
Rt retention time
TFA trifluoroacetic acid
THF tetrahydrofuran

EXAMPLES AND INTERMEDIATE COMPOUNDS

Experimental Methods

Reactions were conducted at room temperature unless otherwise specified. Preparative chromatography was performed using a Flash Master Personal system equipped with Isolute Flash II silica columns or using a CombiFlash Companion system equipped with GraceResolv silica column. The purest fractions were collected, concentrated and dried under vacuum. Compounds were typically dried in a vacuum oven at 40° C. prior to purity analysis. Compound analysis was performed by HPLC/LCMS using an Agilent 1100 HPLC system/Waters ZQ mass spectrometer connected to an Agilent 1100 HPLC system with a Phenomenex Synergi, RP-Hydro column (150×4.6 mm, 4 µm, 1.5 mL per min, 30° C., gradient 5-100% MeCN (+0.085% TFA) in water (+0.1% TFA) over 7 min, 200-300 nm). The compounds prepared were named using IUPAC nomenclature. Accurate masses were measured using a Waters QTOF electrospray ion source and corrected using Leucine Enkephalin lockmass. Spectra were acquired in positive and negative electrospray mode. The acquired mass range was m/z 100-1000. Samples were dissolved in DMSO to give 1 mg/mL solutions which were then further diluted with Acetonitrile (50%)/Water (50%) to 1 µg/mL solutions prior to analysis. The values reported correspond either to the protonated or deprotonated molecular ions [MH]⁺ or [MH]⁻.

Intermediate 1

N-[(3S,4S)-6-Acetyl-2,2-dimethyl-3-[(methylsulfanyl)methoxy]-3,4-dihydro-2H-1-benzopyran-4-yl]-3-chloro-4-fluorobenzamide

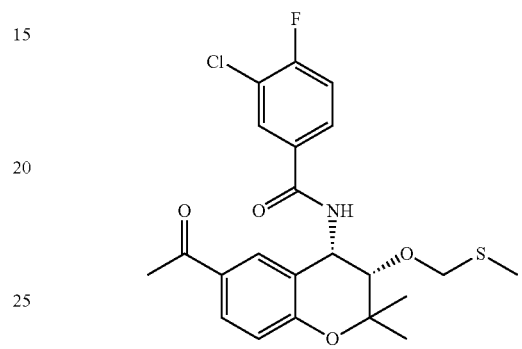

N-[(3S,4S)-6-Acetyl-3-hydroxy-2,2-dimethyl-3,4-dihydro-2H-1-benzopyran-4-yl]-3-chloro-4-fluorobenzamide (1.00 g, 2.55 mmol) was dissolved in DME (10 mL) and added to a suspension of sodium hydride (60% dispersion in oil, 112 mg, 2.81 mmol) in DME (10 mL). The reaction mixture was stirred for 10 min then sodium iodide (421 mg, 2.81 mmol) was added followed by chloromethyl methyl sulfide (232 µL, 2.81 mmol). The reaction mixture was stirred for 18 h then quenched with saturated aqueous ammonium carbonate solution (5 mL), diluted with EtOAc (50 mL), washed with water (3×25 mL), dried (MgSO$_4$) and concentrated in vacuo. The residue was purified by column chromatography on normal phase silica eluting with a gradient of EtOAc in heptane to give the title compound (405 mg, 35.1%) as a white solid. LCMS (ES⁺): 452.1 [MH]+. HPLC: Rt 6.36 min, 86.2% purity.

Intermediate 2

2-{[(tert-Butoxy)carbonyl](propyl)amino}acetic acid

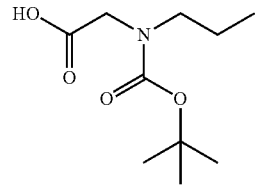

Glyoxylic acid monohydrate (4.67 g, 5.08 mmol) and 1-propylamine (1.50 g, 25.4 mmol) were dissolved in DCM (100 mL) and the reaction mixture was stirred for 18 h and concentrated in vacuo. 1M aq HCl (125 mL, 125 mmol) was added and the reaction mixture was heated under reflux overnight, concentrated in vacuo and crystallised from i-PrOH/Et$_2$O to give a white solid. The 2-(propylamino) acetic acid hydrochloride intermediate (2.49 g, 16.2 mmol), di-tert-butyl dicarbonate (8.84 g, 40.5 mmol) and Et$_3$N (11.3 mL, 81.1 mmol) were dissolved in water (65 mL) and stirred for 3d. The reaction mixture was washed with hexane and the aqueous fraction was acidified with 2M aq HCl and extracted into EtOAc, washed with brine, dried (MgSO₄) and concentrated in vacuo to give the title compound (3.40 g, 61.9%) as a colourless oil. LCMS (ES⁻): 216.1 [MH]⁻.

Example 1

{[(3S,4S)-6-Acetyl-4-[(3-chloro-4-fluorobenzene) amido]-2,2-dimethyl-3,4-dihydro-2H-1-benzopyran-3-yl]oxy}phosphonic acid

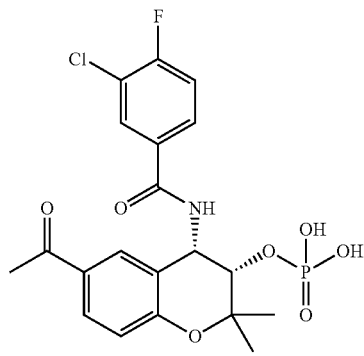 [SMILES: CC(=O)c1ccc2c(c1)[C@H](NC(=O)c1ccc(F)c(Cl)c1)[C@H](OP(=O)(O)O)C(C)(C)O2]

N-[(3S,4S)-6-Acetyl-3-hydroxy-2,2-dimethyl-3,4-dihydro-2H-1-benzopyran-4-yl]-3-chloro-4-fluorobenzamide (2.00 g, 5.10 mmol) was dissolved in methylethyl ketone (50 mL). Pyridine (1.62 mL, 20.4 mmol) and POCl₃ (1.50 mL, 16.3 mmol) were added and the reaction mixture was stirred for 16 h. A precipitate was removed by filtration, washed with methylethyl ketone (50 mL) and 2M aq HCl (10 mL) added to the combined methylethyl ketone phases. The reaction mixture was heated at 65° C. for 1 h. The organic phase was washed with brine (10 mL), dried (MgSO₄) and concentrated in vacuo. The residue was dissolved in EtOAc (50 mL) and stirred for 30 min. The resulting precipitate was collected by filtration, washed with EtOAc (20 mL) and the solid dried in vacuo to give the title compound (1.67 g, 69.3%) as a white solid. LCMS (ES⁺): 471.9 [MH]⁺. HPLC: Rt 4.84 min, 100% purity. HRMS (ESI−) calcd for C₂₀H₂₀ClFNO₇P 470.057. Found 470.057.

Example 2

(3S,4S)-6-Acetyl-4-[(3-chloro-4-fluorobenzene) amido]-2,2-dimethyl-3,4-dihydro-2H-1-benzopyran-3-yl 2-(dimethylamino)acetate hydrochloride

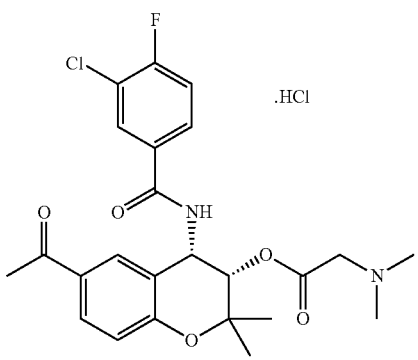 [SMILES: CC(=O)c1ccc2c(c1)[C@H](NC(=O)c1ccc(F)c(Cl)c1)[C@H](OC(=O)CN(C)C)C(C)(C)O2 ; ".HCl"]

N-[(3S,4S)-6-Acetyl-3-hydroxy-2,2-dimethyl-3,4-dihydro-2H-1-benzopyran-4-yl]-3-chloro-4-fluorobenzamide (100 mg, 0.26 mmol) was dissolved in THF (10 mL). Et₃N (78.3 μL, 0.56 mmol), DMAP (3 mg, catalytic) and dimethylaminoacetyl chloride hydrochloride (40.3 mg, 0.26 mmol) were added and the reaction mixture was stirred for 16 h. Further Et₃N (78.3 μL, 0.56 mmol) and dimethylaminoacetyl chloride hydrochloride (40.3 mg, 0.26 mmol) were added and the reaction mixture was stirred for 1 h. Further Et₃N (157 μL, 1.12 mmol) and dimethylaminoacetyl chloride hydrochloride (80.6 mg, 0.52 mmol) were added and the reaction mixture was stirred for 1 h. The reaction mixture was filtered, washed with THF (30 mL) and the filtrates diluted with EtOAc (70 mL). The organic phase was washed with saturated aqueous NaHCO₃ (2×30 mL), dried (MgSO₄) and concentrated in vacuo. The residue was dissolved in Et₂O (10 mL). 2M HCl in Et₂O (2 mL) was added and the resulting precipitate was collected by filtration, washed with Et₂O (10 mL) and dried in vacuo to give the title compound (50.0 mg, 41.1%) as an off-white solid. LCMS (ES⁺): 476.9 [MH]⁺. HPLC: Rt 5.14 min, 97.9% purity. HRMS (ESI+) calcd for C₂₄H₂₆ClFN₂O₅ 477.159. Found 477.158.

Example 3

(3S,4S)-6-Acetyl-4-[(3-chloro-4-fluorobenzene) amido]-2,2-dimethyl-3,4-dihydro-2H-1-benzopyran-3-yl acetate

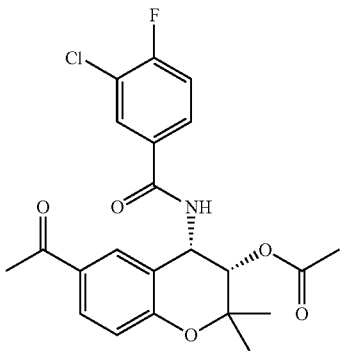 [SMILES: CC(=O)O[C@H]1[C@@H](NC(=O)c2ccc(F)c(Cl)c2)c2cc(C(C)=O)ccc2OC1(C)C]

N-[(3S,4S)-6-Acetyl-3-hydroxy-2,2-dimethyl-3,4-dihydro-2H-1-benzopyran-4-yl]-3-chloro-4-fluorobenzamide (200 mg, 0.51 mmol) was slurried in toluene (2.0 mL) with acetic anhydride (50 μL, 0.51 mmol), N-hydroxysuccinimide (18 mg, 0.15 mmol) and 4-dimethylaminopyridine (6 mg, 0.05 mmol). The reaction mixture was heated to 80° C. for 195 min to give a colourless solution and then cooled to ambient temperature overnight. The reaction mixture was diluted with toluene (2 mL) and washed with 10% aqueous citric acid (4 mL) and water (4 mL). The toluene phase was evaporated in vacuo. The residue was purified by column chromatography on normal phase silica eluting with heptane/ethyl acetate mixtures. The product was crystallised from toluene (1 mL)/heptane (3 mL) overnight. The solid was collected by filtration, washed with heptane (2 mL) and dried in vacuo at 40° C. overnight to give the title compound (88.1 mg, 39.8%) as a white solid. LCMS (ES⁺): 434.0 [MH]⁺. HPLC: Rt 6.32 min, 97.8% purity. HRMS (ESI+) calcd for C₂₂H₂₁ClFNO₅ 434.117. Found 434.117.

Example 4

{[(3S,4S)-6-Acetyl-4-[(3-chloro-4-fluorobenzene)amido]-2,2-dimethyl-3,4-dihydro-2H-1-benzopyran-3-yl]oxy}methyl acetate

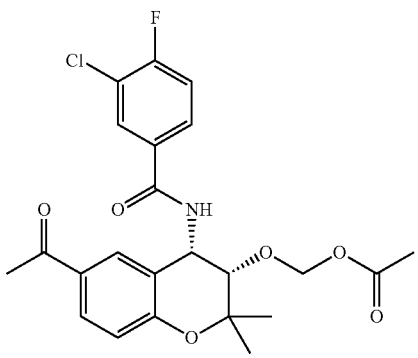 [SMILES: CC(=O)OCO[C@H]1[C@@H](NC(=O)c2ccc(F)c(Cl)c2)c2cc(C(C)=O)ccc2OC1(C)C]

N-[(3S,4S)-6-Acetyl-3-hydroxy-2,2-dimethyl-3,4-dihydro-2H-1-benzopyran-4-yl]-3-chloro-4-fluorobenzamide (229 mg, 0.58 mmol) was stirred in DMF (4.0 mL) with NaH (60% dispersion, 45 mg, 0.68 mmol) for 20 min. Bromomethyl acetate (69 µL, 0.70 mmol) was added and the mixture stirred at room temperature for 90 min. The reaction mixture was quenched with water (8 mL) and extracted with EtOAc (2×5 mL). The combined organic extracts were washed with water (5 mL) and the organic phase evaporated in vacuo. The residue was purified by column chromatography on normal phase silica eluting with 4:1 heptane:EtOAc to give the title compound (88 mg; 32.5%) as a white solid. LCMS (ES+): 464.0 [MH]+. HPLC: Rt 6.52 min, 97.3% purity. HRMS (ESI+) calcd for $C_{23}H_{23}ClFNO_6$ 464.128. Found 464.130.

Example 5

{[(3S,4S)-6-Acetyl-4-[(3-chloro-4-fluorobenzene)amido]-2,2-dimethyl-3,4-dihydro-2H-1-benzopyran-3-yl]oxy}methyl 2-(dimethylamino)acetate

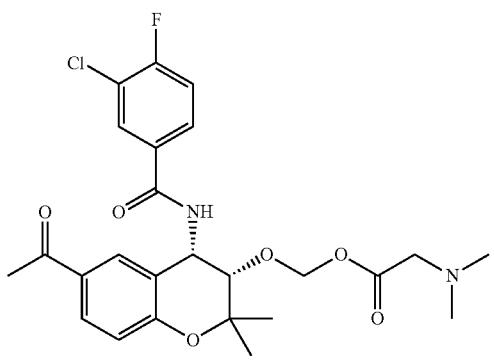 [SMILES: CC(=O)c1ccc2c(c1)[C@H](NC(=O)c1ccc(F)c(Cl)c1)[C@H](OCOC(=O)CN(C)C)C(C)(C)O2]

Intermediate 1 (261 mg, 0.58 mmol) was dissolved in DCM (7 mL) and treated with sulfuryl chloride (51.5 µL, 0.64 mmol). The reaction mixture was stirred for 10 min. N,N-Dimethylglycine (298 mg, 2.89 mmol) and DIPEA (1.00 mL, 5.78 mmol) were dissolved in DCM (3 mL) and added to the reaction mixture. After 30 min the reaction mixture was poured into 1M aqueous $Na_2CO_3$ (50 mL) and extracted with DCM (2×50 mL). The combined organic layers were dried ($MgSO_4$) and concentrated in vacuo. The residue was purified by column chromatography on normal phase silica eluting with a gradient of EtOAc in heptane. The pure fractions were combined and dried in vacuo overnight to give the title compound (114 mg, 38.9%) as a white solid. LCMS (ES+): 507.1 [MH]+. HPLC: Rt 4.99 min, 98.3% purity. HRMS (ESI+) calcd for $C_{26}H_{28}ClFN_2O_6$ 507.170. Found 507.171.

Example 6

(3S,4S)-6-Acetyl-4-[(3-chloro-4-fluorobenzene)amido]-2,2-dimethyl-3,4-dihydro-2H-1-benzopyran-3-yl 2-aminoacetate hydrochloride

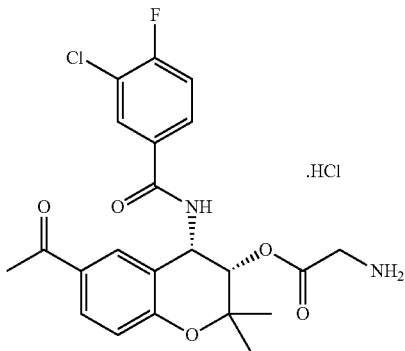 [SMILES: CC(=O)c1ccc2c(c1)[C@H](NC(=O)c1ccc(F)c(Cl)c1)[C@H](OC(=O)CN)C(C)(C)O2 ; ".HCl"]

N-[(3S,4S)-6-Acetyl-3-hydroxy-2,2-dimethyl-3,4-dihydro-2H-1-benzopyran-4-yl]-3-chloro-4-fluorobenzamide (400 mg, 1.02 mmol) was dissolved in DCM (8 mL) at room temperature. Boc-Gly-OSu (full name: 2,5-dioxopyrrolidin-1-yl 2-{[(tert-butoxy)carbonyl]amino}acetate) (556 mg, 2.04 mmol), DIPEA (3914, 2.25 mmol) and DMAP (12 mg, 0.10 mmol) were added. The reaction mixture was stirred overnight. The DCM was evaporated in vacuo and the residue suspended between EtOAc (15 mL) and 10% aqueous citric acid solution (10 mL). The organic phase was washed with water (10 mL) and concentrated in vacuo. The residue was purified by column chromatography on normal phase silica eluting with heptane/EtOAc mixtures. The (3S,4S)-6-acetyl-4-[(3-chloro-4-fluorobenzene)amido]-2,2-dimethyl-3,4-dihydro-2H-1-benzopyran-3-yl 2-{[(tert-butoxy)carbonyl]amino}acetate intermediate was dissolved in 4M HCl in dioxane (4 mL) and stirred at room temperature for 90 min. The solvents were removed in vacuo and the residue partitioned between EtOAc (10 mL) and saturated aqueous $Na_2CO_3$ solution (5 mL). The aqueous layer was extracted with EtOAc (10 mL) and the combined organic phases concentrated in vacuo. The residue was purified by column chromatography on normal phase silica eluting with heptane/ethyl acetate mixtures. To each pure fraction was added 1.25M HCl in EtOH (200 µL). The pure fractions were combined and dried in vacuo to give the title compound (93 mg, 18.8%) as a white foam. LCMS (ES+): 449.0 [MH]+. HPLC: Rt 4.95 min, 96.9% purity. HRMS (ESI+) calcd for $C_{22}H_{22}ClFN_2O_5$ 449.128. Found 449.130.

Example 7

(3S,4S)-6-acetyl-4-[(3-chloro-4-fluorobenzene) amido]-2,2-dimethyl-3,4-dihydro-2H-1-benzopyran-3-yl 2-(methylamino)acetate hydrochloride

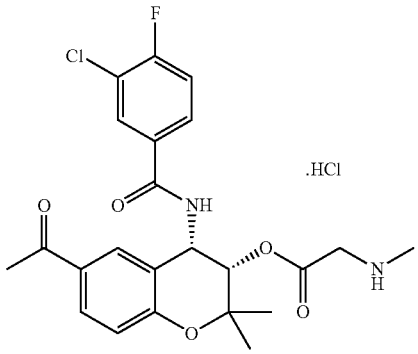 [SMILES: CNCC(=O)O[C@H]1[C@@H](NC(=O)c2ccc(F)c(Cl)c2)c2cc(C(C)=O)ccc2OC1(C)C ; ".HCl"]

N-[(3S,4S)-6-Acetyl-3-hydroxy-2,2-dimethyl-3,4-dihydro-2H-1-benzopyran-4-yl]-3-chloro-4-fluorobenzamide (200 mg, 0.51 mmol) was dissolved in THF (4 mL) at room temperature. Boc-Sar-OSu (full name: tert-butyl N-{2-[(2,5-dioxopyrrolidin-1-yl)oxy]-2-hydroxyethyl}-N-methylcarbamate) (292 mg, 1.02 mmol), DIPEA (196 µL, 1.12 mmol) and DMAP (6 mg, 0.05 mmol) were added and the reaction mixture was stirred overnight at 70° C. The THF was evaporated in vacuo and the residue suspended between EtOAc (10 mL) and 10% aqueous citric acid solution (5 mL). The organic phase was washed with water (10 mL) and concentrated in vacuo. The residue was purified by column chromatography on normal phase silica eluting with heptane/EtOAc mixtures. The (3S,4S)-6-acetyl-4-[(3-chloro-4-fluorobenzene)amido]-2,2-dimethyl-3,4-dihydro-2H-1-benzopyran-3-yl 2-{[(tert-butoxy)carbonyl](methyl)amino}acetate intermediate was dissolved in 4M HCl in dioxane (2 mL) and stirred at room temperature for 1 h. The solvents were removed in vacuo. The residue was triturated in EtOAc/MTBE mixture and then stirred with ice bath cooling for 1 h. The solid was collected by filtration, washed with MTBE (2 mL) and dried in vacuo at 50° C. to give the title compound (110 mg, 43.2%) as a white solid. LCMS (ES+): 463.1[MH]$^E$. HPLC: Rt 5.06 min, 98.6% purity. HRMS (ESI+) calcd for $C_{23}H_{24}ClFN_2O_5$ 463.144. Found 463.144.

Example 8

({[(3S,4S)-6-Acetyl-4-[(3-chloro-4-fluorobenzene)amido]-2,2-dimethyl-3,4-dihydro-2H-1-benzopyran-3-yl]oxy}methoxy)phosphonic acid diamine

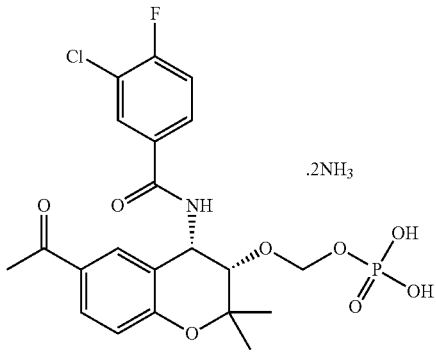 [SMILES: CC(=O)c1ccc2c(c1)[C@H](NC(=O)c1ccc(F)c(Cl)c1)[C@H](OCOP(=O)(O)O)C(C)(C)O2 ; ".2NH3"]

Intermediate 1 (600 mg, 1.33 mmol) was dissolved in THF (12 mL) and treated with phosphoric acid (85%, 911 mg, 9.29 mmol) and powdered 4 Å molecular sieves (1.80 g) at room temperature. The reaction mixture was cooled in an ice bath and N-iodosuccinimide (478 mg; 2.12 mmol) added. The reaction mixture was stirred in an ice bath for 5 min. After overnight at room temperature the reaction mixture was diluted with EtOAc (30 mL). The molecular sieves were removed by filtration and washed with EtOAc (10 mL). The combined organic filtrates were washed with 5% aqueous sodium thiosulfate solution (25 mL). The product was extracted into 10% aqueous sodium carbonate solution (30 mL). The aqueous phase was separated, adjusted to pH1-2 with 2N HCl in ice and the product extracted into EtOAc (15 mL). The organic phase was washed with water (3×10 mL) until pH 4 and then concentrated in vacuo. The residue was partitioned between EtOAc (20 mL) and 5% aqueous sodium carbonate solution (20 mL). The aqueous phase was separated, adjusted to pH 1 with 2N HCl in ice, loaded onto a preconditioned column of Amberlite XAD-4 resin (5 g) and the product eluted with water/MeCN mixtures. The solvents were removed in vacuo and the residue triturated in EtOAc/MTBE mixture. The solid was collected by filtration, washed with MTBE and dried. The solid was partitioned between water (10 mL) and EtOAc (5 mL). 7N Ammonia in MeOH (1 mL) was added. The aqueous phase was separated, concentrated in vacuo, triturated with EtOAc (2×5 mL) and dried in vacuo at 40° C. to give the title compound (44 mg, 6.18%) as a white solid. HPLC: Rt 4.88 min, 98.5% purity. HRMS (ESI–) calcd for $C_{21}H_{22}ClFNO_8P$ 500.068. Found 500.069.

Example 9

(3S,4S)-6-Acetyl-4-[(3-chloro-4-fluorobenzene)amido]-2,2-dimethyl-3,4-dihydro-2H-1-benzopyran-3-yl(2S)-2-amino-4-methylpentanoate hydrochloride

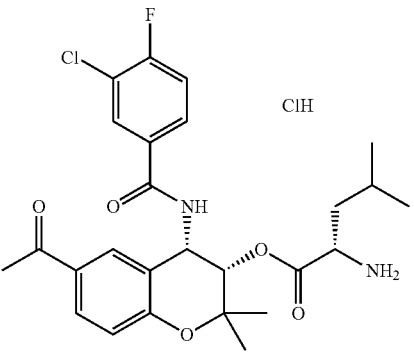 [SMILES: CC(=O)c1ccc2c(c1)[C@H](NC(=O)c1ccc(F)c(Cl)c1)[C@H](OC(=O)[C@@H](N)CC(C)C)C(C)(C)O2 ; Cl]

Boc-Leu-OH (full name: (2S)-2-{[(tert-butoxy)carbonyl]amino}-4-methylpentanoic acid) (555 mg, 2.40 mmol), HOBt hydrate (429 mg, 2.80 mmol), EDC.HCl (537 mg, 2.80 mmol) and DMAP (733 mg, 6.00 mmol) were dissolved in DCM (15 mL) and the reaction mixture was stirred for 15 min. N-[(3S,4S)-6-Acetyl-3-hydroxy-2,2-dimethyl-3,4-dihydro-2H-1-benzopyran-4-yl]-3-chloro-4-fluorobenzamide (784 mg, 2.00 mmol) was added and the reaction mixture was stirred for 4d, diluted with EtOAc, washed with 10% aq citric acid, 10% aq $NaHCO_3$ and brine, dried ($MgSO_4$) and concentrated in vacuo. This procedure was repeated on the same scale and the combined reaction products were purified by column chromatography on normal phase silica eluting with hexane/EtOAc mixtures. The (3S,4S)-6-acetyl-4-[(3-chloro-4-fluorobenzene)amido]-2,2-dimethyl-3,4-dihydro-2H-1-benzopyran-3-yl(2S)-2-{[(tert-butoxy)carbonyl]amino}-4-methylpentanoate intermediate (520 mg, 0.86 mmol) was dissolved in DCM (10 mL) and 4N HCl in dioxane (4.3 mL) was added. The reaction mixture was stirred until completion, diluted with EtOAc, washed with 1M aq NaOH, water and brine, dried ($MgSO_4$) and concentrated in vacuo. The residue was dissolved in Et$_2$O and acidified with 2M HCl in Et$_2$O, and the resulting precipitate was collected by filtration, washed with Et$_2$O and dried in vacuo at 40° C. to give the title compound (273 mg, 12.9%) as a white solid. LCMS (ES$^+$): 505.1 [MH]$^+$. HPLC: Rt 5.57 min, 99.2% purity. HRMS (ESI+) calcd for C$_{26}$H$_{30}$ClFN$_2$O$_5$ 505.191. Found 505.188.

Example 10

(3S,4S)-6-Acetyl-4-[(3-chloro-4-fluorobenzene)amido]-2,2-di methyl-3,4-dihydro-2H-1-benzopyran-3-yl 2-(propylamino)acetate hydrochloride

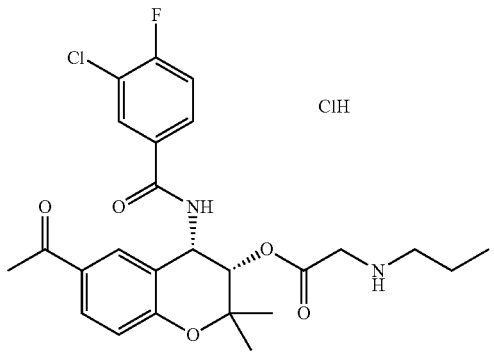 [SMILES: CCCNCC(=O)O[C@H]1[C@@H](NC(=O)c2ccc(F)c(Cl)c2)c2cc(C(C)=O)ccc2OC1(C)C ; Cl]

Intermediate 2 (478 mg, 2.20 mmol), HOBt hydrate (429 mg, 2.80 mmol), EDC.HCl (537 mg, 2.80 mmol) and DMAP (733 mg, 6.00 mmol) were dissolved in DCM (15 mL) and the reaction mixture was stirred for 15 min. N-[(3S,4S)-6-Acetyl-3-hydroxy-2,2-dimethyl-3,4-dihydro-2H-1-benzopyran-4-yl]-3-chloro-4-fluorobenzamide (784 mg, 2.00 mmol) was added and the reaction mixture was stirred for 24 h, diluted with EtOAc, washed with 1M aq HCl, 10% aq NaHCO$_3$ and brine, dried (MgSO$_4$) and concentrated in vacuo. The residue was purified by column chromatography on normal phase silica eluting with hexane/EtOAc 3:1. The (3S,4S)-6-acetyl-4-[(3-chloro-4-fluorobenzene)amido]-2,2-dimethyl-3,4-dihydro-2H-1-benzopyran-3-yl 2-{[(tert-butoxy)carbonyl](propyl)amino}acetate intermediate (360 mg, 0.61 mmol) was dissolved in DCM (6 mL) and 4N HCl in dioxane (3 mL) was added. The reaction mixture was stirred until completion, diluted with EtOAc, washed with 1M aq NaOH, water and brine, dried (MgSO$_4$) and concentrated in vacuo. The residue was dissolved in Et$_2$O and acidified with 2M HCl in Et$_2$O, and the resulting precipitate was collected by filtration, washed with Et$_2$O and dried in vacuo at 40° C. to give the title compound (261 mg, 25.9%) as a white solid. LCMS (ES$^+$): 491.1 [MH]$^+$. HPLC: Rt 5.35 min, 98.7% purity. HRMS (ESI+) calcd for C$_{25}$H$_{28}$ClFN$_2$O$_5$ 491.175. Found 491.177.

Example 11

(3S,4S)-6-Acetyl-4-[(3-chloro-4-fluorobenzene)amido]-2,2-di methyl-3,4-dihydro-2H-1-benzopyran-3-yl 2-[(propan-2-yl)amino]acetate hydrochloride

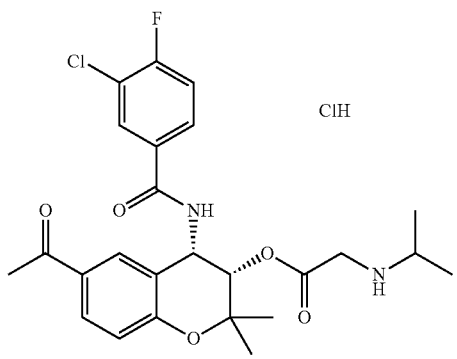 [SMILES: CC(=O)c1ccc2c(c1)[C@H](NC(=O)c1ccc(F)c(Cl)c1)[C@H](OC(=O)CNC(C)C)C(C)(C)O2 ; Cl]

N-Boc-N-isopropylamino-acetic acid (520 mg, 2.39 mmol), HOBt hydrate (441 mg, 2.88 mmol), EDC.HCl (552 mg, 2.88 mmol) and DMAP (733 mg, 6.00 mmol) were dissolved in DCM (10 ml) and the reaction mixture was stirred for 30 min. N-[(3S,4S)-6-Acetyl-3-hydroxy-2,2-dimethyl-3,4-dihydro-2H-1-benzopyran-4-yl]-3-chloro-4-fluorobenzamide (784 mg, 2.00 mmol) was added and the reaction mixture was stirred for 20 h and concentrated in vacuo. The residue was purified by column chromatography on normal phase silica eluting with hexane/EtOAc 3:1. The (3S,4S)-6-acetyl-4-[(3-chloro-4-fluorobenzene)amido]-2,2-dimethyl-3,4-dihydro-2H-1-benzopyran-3-yl 2-{[(tert-butoxy)carbonyl](propan-2-yl)amino}acetate intermediate (820 mg, 1.39 mmol) was dissolved in MeOH (3 mL) and 4N HCl in dioxane (20 mL) was added. The reaction mixture was stirred for 2 h and concentrated in vacuo. The residue was suspended in diisopropyl ether (50 mL) and EtOAc (1 mL), stirred overnight and collected by filtration. The residue was partitioned between aq NaHCO$_3$ (20 mL) and DCM (20 mL) and the aqueous fraction was extracted with DCM (2×20 mL). The combined organic fractions were concentrated in vacuo and the residue was purified by normal phase silica eluting with hexane/EtOAc 1:2. The residue was suspended in Et$_2$O (6 mL) and 2M HCl in Et$_2$O (2 mL), stirred for 1 h and the precipitate was collected by filtration and washed with Et$_2$O (2×2 mL) to give the title compound (451 mg, 43.2% in two batches) as a white solid. LCMS (ES$^+$): 491.1 [MH]$^+$. HPLC: Rt 5.23-5.24 min, 99.5-100% purity. HRMS (ESI+) calcd for C$_{25}$H$_{28}$ClFN$_2$O$_5$ 491.175. Found 491.173.

Preparation of Compounds of Formula (II)

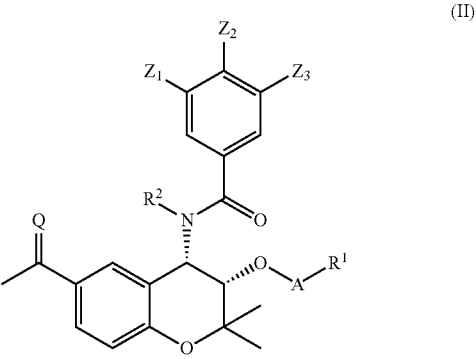

(II)

Scheme 3. General synthetic route for preparation of compounds of formula (IIa)

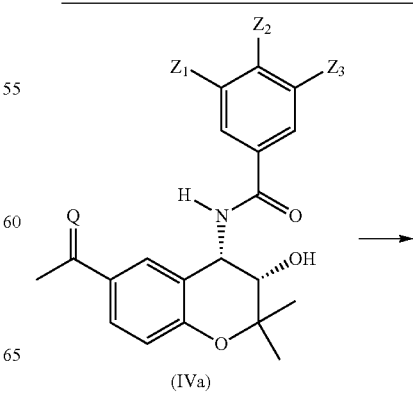

(IVa)

-continued

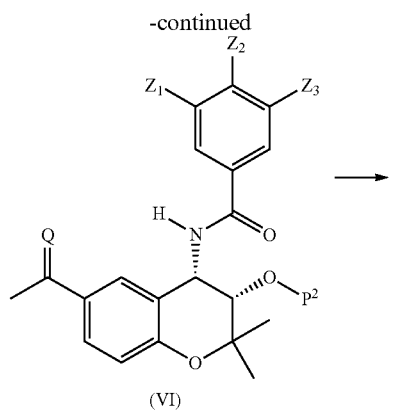

(VI)

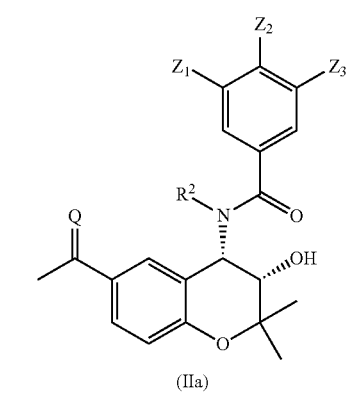

(VII)

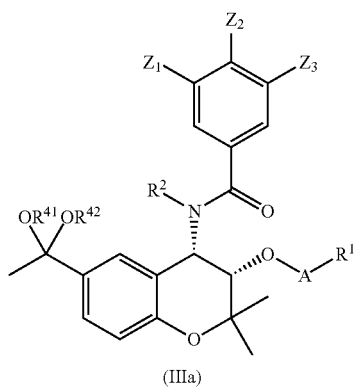

(IIa)

wherein Q, $Z_1$, $Z_2$, $Z_3$ and $R^2$ are as defined in the section entitled "detailed description of the invention" and $P^2$ is a suitable protecting group.

Compounds of general formula (IIa) can easily be prepared from the alcohols of general formula (IVa) by protecting the hydroxyl functionality with a suitable protecting group $P^2$ to give compounds of general formula (VI) and then coupling the prodrug functionality onto the amide nitrogen atom in one or more steps using synthetic strategies analogous to those used for the synthesis of compounds of general formula (I). The final step is to remove the protecting group $P^2$ to give compounds of general formula (IIa).

Preparation of Compounds of Formula (IIIa) and (IIIb)

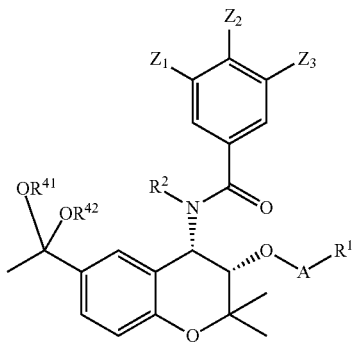

(IIIa)

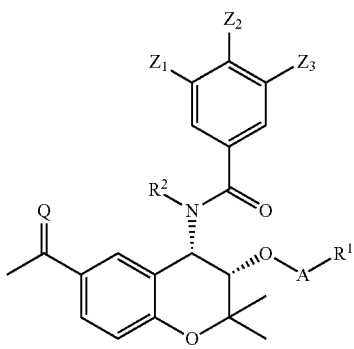

(IIIb)

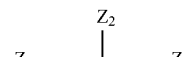

Scheme 4. General synthetic route for preparation of compounds of formula (IIIa)

(Id)

(IIIa)

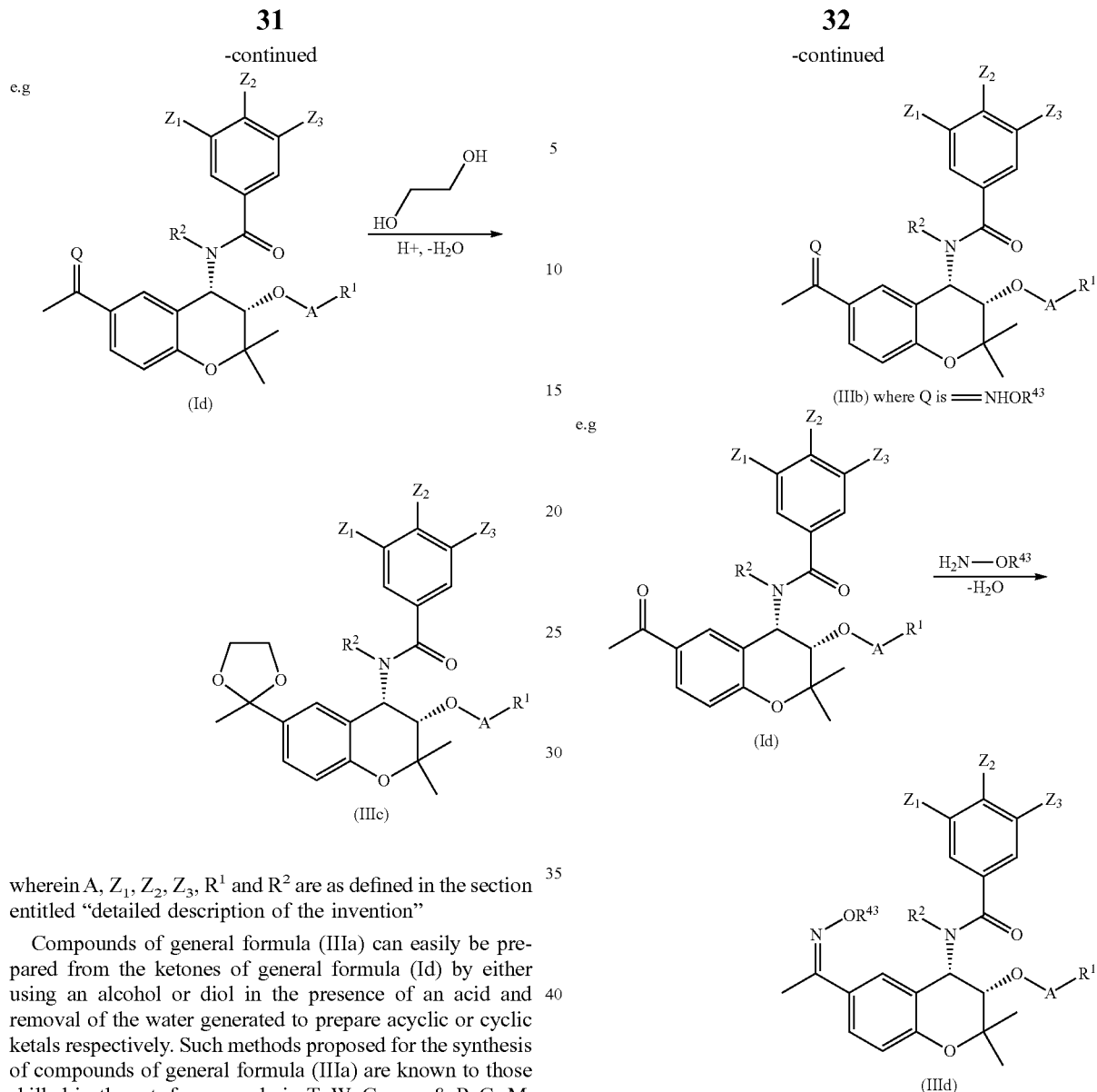

wherein A, $Z_1$, $Z_2$, $Z_3$, $R^1$ and $R^2$ are as defined in the section entitled "detailed description of the invention"

Compounds of general formula (IIIa) can easily be prepared from the ketones of general formula (Id) by either using an alcohol or diol in the presence of an acid and removal of the water generated to prepare acyclic or cyclic ketals respectively. Such methods proposed for the synthesis of compounds of general formula (IIIa) are known to those skilled in the art, for example in T. W. Greene & P. G. M. Wuts, Protective Groups in Organic Synthesis (2nd edition) J. Wiley & Sons, 1991 and P. J. Kocienski, Protecting Groups, Georg Thieme Verlag, 1994.

Scheme 5. General synthetic routes for preparation of compounds of formula (IIIb)

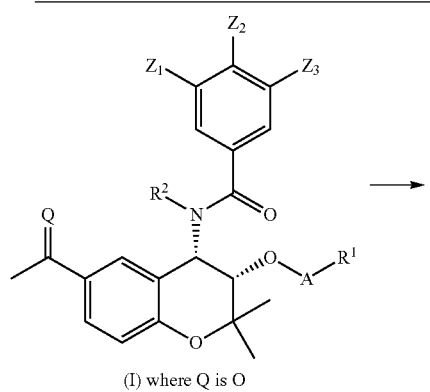

wherein A, Q, $Z_1$, $Z_2$, $Z_3$, $R^1$, $R^2$, and $R^{43}$ are as defined in the section entitled "detailed description of the invention"

Compounds of general formula (IIIb) can easily be prepared from the ketones of general formula (I) where Q=O by using the appropriate hydroxylamine and removal of the water generated to prepare the ketoxime. Such methods proposed for the synthesis of compounds of general formula (IIIb) are known to those skilled in the art, for example in T. W. Greene & P. G. M. Wuts, Protective Groups in Organic Synthesis (2nd edition) J. Wiley & Sons, 1991

Biological Rational

Without wishing to be bound by theory, the general mode of action of the claimed pro-drugs is as follows. For IV administration the high solubility conferred by the solubilising pro-moiety to the parent Tonabersat-like drug is expected to allow a rapid bolus injection whereupon the pro-drug will be quickly cleaved by in vivo esterases/phosphatases to reveal the parent drug. For PO administration the preferred mode of action is where the solubilising pro-drug is predominantly cleaved in the gut by esterases/phosphatases prior to absorption of the parent drug into the systemic circulation, or where the solubilising pro-drug is absorbed intact and then quickly cleaved by plasma esterases/phosphatases to reveal the parent drug.

Solubility

In an embodiment, prodrugs of the present invention are suitable for oral administration. The skilled person understands that the pH of the gastrointestinal tract changes along its length. For example, the stomach has a pH of around pH 1.5 and the GI tract after the stomach has a pH of around 5 to 7.5. For more detail see, for example, *Measurement of gastrointestinal pH profiles in normal ambulant human subjects*, Gut. 1988 August; 29(8): 1035-1041. Improved solubility is expected to result in improved absorption, and therefore improved oral bioavailability. Thus improved solubility at any pH value between around pH 1.5 to 8 is expected to improve oral bioavailability. Compounds of the invention were assessed for solubility in aqueous solutions having a pH of from 2 to 10. In an embodiment prodrugs of the invention have a solubility of >0.5 mg/mL in an aqueous solution having a pH of from 2 to 10, including from 2 to 8. In an embodiment prodrugs have a solubility of >5.0 mg/mL, or >10.0 mg/mL, >100.0 mg/mL, or >200.0 mg/mL in an aqueous solution having a pH of from 2 to 10, including from 2 to 8. In an embodiment the prodrugs have the aforementioned aqueous solubility at a pH within the range of from 4 to 8, or from 6 to 8.

In an embodiment, prodrugs of the invention are administered intravenously. High prodrug solubility is advantageous in order to reduce the volume of solution administered to the patient, and to reduce the risk of damage to the circulatory system. Solubility in an aqueous solution having a pH of from 2 to 10 of >10 mg/mL is preferred. Yet more preferred is solubility in an aqueous solution having a pH of from 2 to 10 of >30 mg/mL or >100.0 mg/mL. Yet more preferred is solubility in an aqueous solution having a pH of from 2 to 10 of >200.0 mg/mL. The solubility is measured in an aqueous solution having a pH of from 2 to 10, which pH range is advantageous for intravenous prodrug delivery. See, for example, *A guide on intravenous drug compatibilities based on their pH*, Nasser S C et al./Pharmacie Globale (IJCP) 2010, 5 (01)). In an embodiment the prodrugs of the claimed invention have solubility of >10 mg/mL in an aqueous solution having a pH of from 2 to 10. In an embodiment the prodrugs have the aforementioned aqueous solubility at a pH within the range of from 2 to 8, or from 4 to 8, or from 6 to 8. The solubility of the Examples is illustrated in Table 1.

Pharmacokinetics

Example prodrugs were dosed either intravenously or orally to fasted male Sprague Dawley rats. The rats underwent surgery for jugular vein cannulation 48 hrs prior to dosing. Following dosing, 0.25 mL blood samples were taken via the cannulae at 0, 5, 10, 20, 30, 45, 60, 120, 240 & 360 minutes in EDTA coated tubes. Tubes were spun at 13,000 rpm for 4 minutes and 100 ul of supernatant taken immediately and stored at −80° C. prior to analysis. Plasma samples were analysed by LC-MS/MS following extraction by protein precipitation, and levels of parent prodrug and tonabersat were measured by MRM (Multiple Reaction Monitoring) analysis against an extracted calibration curve of plasma samples spiked with the Example prodrug and tonabersat.

The exposure of tonabersat in plasma following dosing of the prodrugs of the invention was compared directly to the exposure observed following dosing of an equimolar amount of tonabersat under analogous assay conditions (5.00 mg/kg oral dosing or 0.78 mg/kg intravenous dosing). In an embodiment, prodrugs of the present invention have >10% exposure of tonabersat obtained following either oral or intravenous dosing of the prodrug, compared to the exposure obtained from dosing an equimolar amount of tonabersat itself. In an embodiment the exposure of tonabersat following dosing of the prodrugs is >20%, or >30%, or >40%, or >50% or preferably >70% compared to the exposure obtained from dosing an equimolar amount of tonabersat itself.

Example 2 was dosed according to this protocol at 0.95 mg/kg IV. Plasma levels of Example 2 were found to decline from 730 ng/mL at 5 min to <5 ng/mL at 6 hrs. Plasma levels of tonabersat were determined to be 130 ng/mL at 5 min and 115 ng/mL at 6 hrs clearly showing conversion of the prodrug to tonabersat over this timecourse following intravenous dosing. This corresponds to an exposure of tonabersat following dosing of the prodrug of 64% compared to the exposure obtained from dosing an equimolar amount of tonabersat itself.

Example 2 was dosed according to this protocol at 6.10 mg/kg PO. Plasma levels of Example 2 were found to decline from 38 ng/mL at 5 min to <5 ng/mL at 6 hrs. Plasma levels of tonabersat were determined to be 63 ng/mL at 5 min and 900 ng/mL at 6 hrs clearly showing conversion of the prodrug to tonabersat over this timecourse following oral dosing. This corresponds to an exposure of tonabersat following dosing of the prodrug of 85% compared to the exposure obtained from dosing an equimolar amount of tonabersat itself. Pharmacokinetic data on the Examples is summarized in Table 2.

TABLE 1

| Example | Solubility |
|---|---|
| 1 | >50 mg/mL (pH 5.7) |
| 2 | >20 mg/mL (pH 3.6) |
| 3 | <0.25 (pH 3.5) |
| 4 | <0.25 (pH 3.5) |
| 5 | >2 (pH 3.0) |
| 6 | >20 mg/mL (pH 4.0) |
| 7 | >20 mg/mL (pH 4.4) |
| 8 | >200 mg/mL (pH 5.7) |
| 9 | >5 mg/mL (pH 2.7) |
| 10 | >10 mg/mL (pH 4.4) |
| 11 | >10 mg/mL (pH 4.2) |

TABLE 2

| | % exposure of tonabersat after dosing the prodrugs of the invention via: | |
|---|---|---|
| Example | Oral dosing (po) | Intravenous dosing (iv) |
| 1 | 18% | 40% |
| 2 | 85% | 64% |
| 3 | 22% | 16% |
| 4 | 59% | 47% |
| 5 | Not Tested | Not Tested |
| 6 | 44% | 43% |
| 7 | 40% | 40% |
| 8 | 75% | 58% |
| 9 | 60% | 46% |
| 10 | 56% | 60% |
| 11 | 100% | 63% | hERG Assay

Compounds of the invention were tested for inhibition of the human ether a go-go related gene (hERG) K+ channel using IonWorks patch clamp electrophysiology. 8 Point concentration-response curves were generated on two occasions using 3-fold serial dilutions from the maximum assay concentration (33 uM). Electrophysiological recordings were made from a Chinese Hamster Lung cell line stably expressing the full length hERG channel. Single cell ion currents were measured in the perforated patch clamp configuration (100 ug/mL amphoterocin) at room temperature using an IonWorks Quattro instrument. The internal solution contained 140 mM KCl, 1 mM $MgCl_2$, 1 mM EGTA and 20 mM HEPES and was buffered to pH 7.3. The external solution contained 138 mM NaCl, 2.7 mM KCl, 0.9 mM $CaCl_2$, 0.5 mM $MgCl_2$, 8 mM $Na_2HPO_4$ and 1.5 mM $KH_2PO_4$, and was buffered to pH 7.3. Cells were clamped at a holding potential of 70 mV for 30 s and then stepped to +40 mV for 1 s. This was followed by a hyperpolarising step of 1 s to 30 mV to evoke the hERG tail current. This sequence was repeated 5 times at a frequency of 0.25 Hz. Currents were measured from the tail step at the $5^{th}$ pulse, and referenced to the holding current. Compounds were incubated for 6-7 min prior to a second measurement of the hERG signal using an identical pulse train. A minimum of 17 cells were required for each pIC50 curve fit. A control compound (quinidine) was used.

Example 1 was tested in line with the preceding experimental procedure and shown to have a hERG IC50 of >11 uM.

In an embodiment the compounds of the invention have a hERG IC50 of >11 uM.

The invention claimed is:
1. A compound of formula (I), or a pharmaceutically acceptable salt thereof:

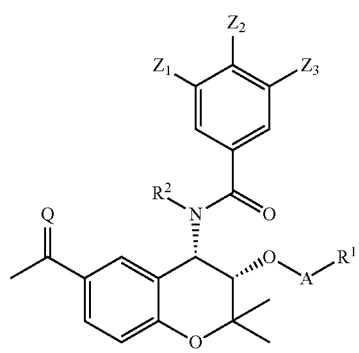

wherein
$Z_1$, $Z_2$, and $Z_3$ are each independently selected from H, F, or Cl;
Q is O;
$R^2$ is H;
A is a direct bond, —C(O)O*—, —C($R^3$)($R^4$)O*—, —C(O)O—C($R^3$)($R^4$)O*—, or —C($R^3$)($R^4$)O—C(O)O*— wherein the atom marked * is directly connected to $R^1$,
$R^3$ and $R^4$ are selected independently from H, fluoro, $C_{1-4}$ alkyl, or $C_{1-4}$ fluoroalkyl, or $R^3$ and $R^4$ together with the atom to which they are attached form a cyclopropyl group; and $R^1$ is selected from groups [1], [2], [2A], [2B], [3], [4], [5] or [6] wherein the atom marked ** is directly connected to A:

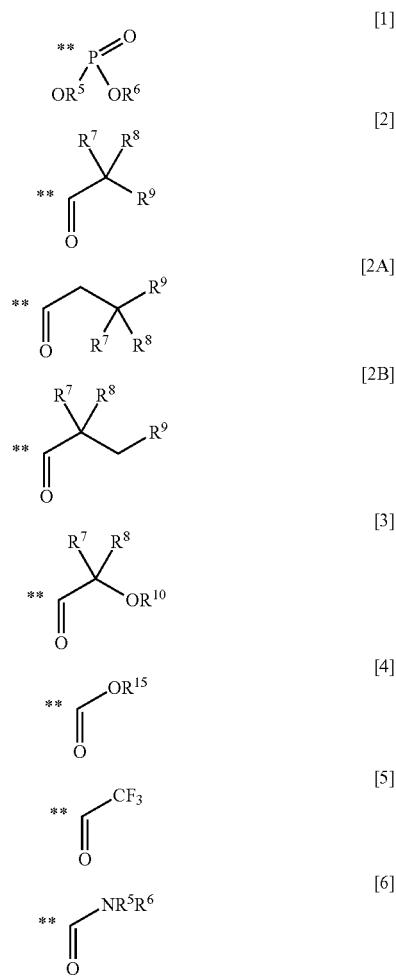

$R^5$ and $R^6$ are independently selected from H, $C_{1-4}$ alkyl, $C_{1-4}$ fluoroalkyl or benzyl;
$R^7$ is independently selected from H, $C_{1-4}$ alkyl, or $C_{1-4}$ fluoroalkyl;
$R^8$ is selected from:
(i) H, $C_{1-4}$ alkyl, or $C_{1-4}$ fluoroalkyl, or
(ii) the side chain of a natural or unnatural alpha-amino acid
or $R^7$ and $R^8$ together with the atom to which they are attached form a $C_{3-7}$ carbocyclic ring;
$R^9$ is selected from H, —N($R^{11}$)($R^{12}$), or —N+($R^{11}$)($R^{12}$)($R^{13}$)X−, or —N($R^{11}$)C(O)$R^{14}$ wherein $R^{11}$, $R^{12}$, and $R^{13}$ are independently selected from H, $C_{1-4}$ alkyl, or $C_{1-4}$ fluoroalkyl, or $R^{11}$ and $R^{12}$ together with the nitrogen atom to which they are attached form a 3-8 membered heterocyclic ring;
$R^{14}$ is H, $C_{1-4}$ alkyl, or $C_{1-4}$ fluoroalkyl;
$R^{10}$ and $R^{15}$ are independently selected from $C_{1-4}$ alkyl or $C_{1-4}$ fluoroalkyl;
X− is a pharmaceutically acceptable anion;
wherein following dosing to a human or animal subject, results in an exposure of tonabersat of greater than 10% compared to the exposure obtained from dosing an equimolar amount of tonabersat.

2. A compound according to claim 1 wherein following dosing to a human or animal subject, results in an exposure of tonabersat of greater than 50% compared to the exposure obtained from dosing an equimolar amount of tonabersat.

3. A compound according to claim 1 wherein A is a direct bond, or —C($R^3$)($R^4$)O*—.

4. A compound according to claim 1 wherein $R^3$ and $R^4$ are both H, or $R^3$ and $R^4$ are both $C_{1-4}$ alkyl, or $R^3$ is H and $R^4$ is $C_{1-4}$ alkyl.

5. A compound according to claim 1 wherein $R^3$ is H and $R^4$ is methyl, ethyl or isopropyl.

6. A compound according to claim 1 wherein -A-$R^1$ has the formula wherein the atom marked ** is directly connected to the oxygen atom:

[chemical structures]

7. A compound according to claim 1 wherein $Z_1$ is Cl, $Z_2$ is F, and $Z_3$ is H; or $Z_1$ is Cl, $Z_2$ and $Z_3$ are H; or $Z_1$ is H, $Z_2$ is F, and $Z_3$ is H; or $Z_1$ is F, $Z_1$ is H, and $Z_3$ is F.

8. A compound according to claim 1 wherein the compound of formula (I) is selected from:
- {[3S,4S)-6-Acetyl-4-[(3-chloro-4-fluorobenzene)amido]-2,2-dimethyl-3,4-dihydro-2H-1-benzopyran-3-yl]oxy}phosphonic acid,
- (3 S,4S)-6-Acetyl-4-[(3-chloro-4-fluorobenzene)amido]-2,2-dimethyl-3,4-dihydro-2H-1-benzopyran-3-yl 2-(dimethylamino)acetate,
- (3 S,4S)-6-Acetyl-4-[(3-chloro-4-fluorobenzene)amido]-2,2-dimethyl-3,4-dihydro-2H-1-benzopyran-3-yl acetate,
- {[(3S,4S)-6-Acetyl-4-[(3-chloro-4-fluorobenzene)amido]-2,2-dimethyl-3,4-dihydro-2H-1-benzopyran-3-yl]oxy}methyl acetate,
- {[(3 S,4S)-6-Acetyl-4-[(3-chloro-4-fluorobenzene)amido]-2,2-dimethyl-3,4-dihydro-2H-1-benzopyran-3-yl]oxy}methyl 2-(dimethylamino)acetate,
- (3 S,4S)-6-Acetyl-4-[(3-chloro-4-fluorobenzene)amido]-2,2-dimethyl-3,4-dihydro-2H-1-benzopyran-3-yl 2-aminoacetate,
- (3 S,4S)-6-acetyl-4-[(3-chloro-4-fluorobenzene)amido]-2,2-dimethyl-3,4-dihydro-2H-1-benzopyran-3-yl 2-(methylamino)acetate,
- ({[(3S,4S)-6-Acetyl-4-[(3-chloro-4-fluorobenzene)amido]-2,2-dimethyl-3,4-dihydro-2H-1-benzopyran-3-yl]oxy}methoxy)phosphonic acid,
- (3S,4S)-6-Acetyl-4-[(3-chloro-4-fluorobenzene)amido]-2,2-dimethyl-3,4-dihydro-2H-1-benzopyran-3-yl (2S)-2-amino-4-methylpentanoate,
- (3S,4S)-6-Acetyl-4-[(3-chloro-4-fluorobenzene)amido]-2,2-dimethyl-3,4-dihydro-2H-1-benzopyran-3-yl 2-(propylamino)acetate,
- (3S,4S)-6-Acetyl-4-[(3-chloro-4-fluorobenzene)amido]-2,2-dimethyl-3,4-dihydro-2H-1-benzopyran-3-yl 2-[(propan-2-yl)amino]acetate, and a pharmaceutically acceptable salt thereof.

9. A pharmaceutical composition comprising a compound of formula (I), or a pharmaceutically acceptable salt thereof:

[structure of formula (I)]

wherein $Z_1$, $Z_2$, and $Z_3$ are each independently selected from H, F, or Cl;

Q is O;

$R^2$ is H;

A is a direct bond, —C(O)O*—, —C($R^3$)($R^4$)O*—, —C(O)O—C($R^3$)($R^4$)O*—, or —C($R^3$)($R^4$)O—C(O)O*— wherein the atom marked * is directly connected to $R^1$, $R^3$ and $R^4$ are selected independently from H, fluoro, $C_{1-4}$ alkyl, or $C_{1-4}$ fluoroalkyl, or $R^3$ and $R^4$ together with the atom to which they are attached form a cyclopropyl group; and $R^1$ is selected from groups [1], [2], [2A], [2B], [3], [4], [5] or [6] wherein the atom marked ** is directly connected to A:

[1] [phosphonate structure with $OR^5$, $OR^6$]

[2] [structure with $R^7$, $R^8$, $R^9$]

[2A] [structure with $R^7$, $R^8$, $R^9$]

[2B] [structure with $R^7$, $R^8$, $R^9$]

-continued

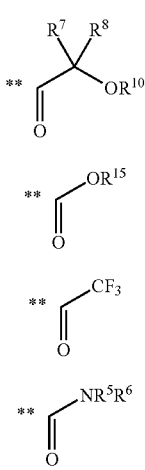

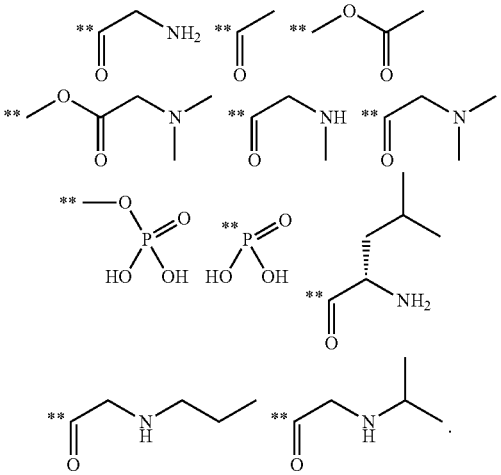

$R^5$ and $R^6$ are independently selected from H, $C_{1-4}$ alkyl, $C_{1-4}$ fluoroalkyl or benzyl;

$R^7$ is independently selected from H, $C_{1-4}$ alkyl, or $C_{1-4}$ fluoroalkyl;

$R^8$ is selected from:

(iii) H, $C_{1-4}$ alkyl, or $C_{1-4}$ fluoroalkyl, or (iv) the side chain of a natural or unnatural alpha-amino acid or $R^7$ and $R^8$ together with the atom to which they are attached form a $C_{3-7}$ carbocyclic ring;

$R^9$ is selected from H, —N($R^{11}$)($R^{12}$), or —N$^+$($R^{11}$)($R^{12}$)($R^{13}$)X$^-$, or —N($R^{11}$)C(O)$R^{14}$ wherein $R^{11}$, $R^{12}$, and $R^{13}$ are independently selected from H, $C_{1-4}$ alkyl, or $C_{1-4}$ fluoroalkyl, or $R^{11}$ and $R^{12}$ together with the nitrogen atom to which they are attached form a 3-8 membered heterocyclic ring;

$R^{14}$ is H, $C_{1-4}$ alkyl, or $C_{1-4}$ fluoroalkyl;

$R^{10}$ and $R^{15}$ are independently selected from $C_{1-4}$ alkyl or $C_{1-4}$ fluoroalkyl;

X$^-$ is a pharmaceutically acceptable anion;

together with one or more pharmaceutically acceptable carriers and/or excipients, wherein following dosing to a human or animal subject, results in an exposure of tonabersat of greater than 10% compared to the exposure obtained from dosing an equimolar amount of tonabersat.

10. A pharmaceutical composition according to claim 9, wherein following dosing to a human or animal subject, results in an exposure of tonabersat of greater than 50% compared to the exposure obtained from dosing an equimolar amount of tonabersat.

11. A pharmaceutical composition according to claim 9, wherein A is a direct bond, or —C($R^3$)($R^4$)O*—.

12. A pharmaceutical composition according to claim 9, wherein $R^3$ and $R^4$ are both H, or $R^3$ and $R^4$ are both $C_{1-4}$ alkyl, or $R^3$ is H and $R^4$ is $C_{1-4}$ alkyl.

13. A pharmaceutical composition according to claim 9, wherein $R^3$ is H and $R^4$ is methyl, ethyl or isopropyl.

14. A pharmaceutical composition according to claim 9, wherein -A-$R^1$ has the formula wherein the atom marked ** is directly connected to the oxygen atom:

15. A pharmaceutical composition according to claim 9, wherein $Z_1$ is Cl, $Z_2$ is F, and $Z_3$ is H; or $Z_1$ is Cl, $Z_2$ and $Z_3$ are H; or $Z_1$ is H, $Z_2$ is F, and $Z_3$ is H; or $Z_1$ is F, $Z_2$ is H, and $Z_3$ is F.

16. A pharmaceutical composition according to claim 9, wherein the compound of formula (I) is selected from:

{[(3S,4S)-6-Acetyl-4-[(3-chloro-4-fluorobenzene)amido]-2,2-dimethyl-3,4-dihydro-2H-1-benzopyran-3-yl]oxy}phosphonic acid, (3S,4S)-6-Acetyl-4-[(3-chloro-4-fluorobenzene)amido]-2,2-dimethyl-3,4-dihydro-2H-1-benzopyran-3-yl 2-(dimethylamino)acetate, (3S,4S)-6-Acetyl-4-[(3-chloro-4-fluorobenzene)amido]-2,2-dimethyl-3,4-dihydro-2H-1-benzopyran-3-yl acetate, {[(3S,4S)-6-Acetyl-4-[(3-chloro-4-fluorobenzene)amido]-2,2-dimethyl-3,4-dihydro-2H-1-benzopyran-3-yl]oxy}methyl acetate, {[(3S,4S)-6-Acetyl-4-[(3-chloro-4-fluorobenzene)amido]-2,2-dimethyl-3,4-dihydro-2H-1-benzopyran-3-yl]oxy}methyl 2-(dimethylamino)acetate, (3S,4S)-6-Acetyl-4-[(3-chloro-4-fluorobenzene)amido]-2,2-dimethyl-3,4-dihydro-2H-1-benzopyran-3-yl 2-aminoacetate, (3S,4S)-6-acetyl-4-[(3-chloro-4-fluorobenzene)amido]-2,2-dimethyl-3,4-dihydro-2H-1-benzopyran-3-yl 2-(methylamino)acetate, ({[(3S,4S)-6-Acetyl-4-[(3-chloro-4-fluorobenzene)amido]-2,2-dimethyl-3,4-dihydro-2H-1-benzopyran-3-yl]oxy}methoxy)phosphonic acid, (3S,4S)-6-Acetyl-4-[(3-chloro-4-fluorobenzene)amido]-2,2-dimethyl-3,4-dihydro-2H-1-benzopyran-3-yl (2S)-2-amino-4-methylpentanoate, (3S,4S)-6-Acetyl-4-[(3-chloro-4-fluorobenzene)amido]-2,2-dimethyl-3,4-dihydro-2H-1-benzopyran-3-yl 2-(propylamino)acetate, (3S,4S)-6-Acetyl-4-[(3-chloro-4-fluorobenzene)amido]-2,2-dimethyl-3,4-dihydro-2H-1-benzopyran-3-yl 2-[(propan-2-yl)amino]acetate, and a pharmaceutically acceptable salt thereof.

* * * * *